(12) United States Patent
Schallner et al.

(10) Patent No.: US 6,864,219 B2
(45) Date of Patent: Mar. 8, 2005

(54) SUBSTITUTED ARYL KETONES

(75) Inventors: Otto Schallner, Monheim (DE); Stefan Lehr, Langenfeld (DE); Hans-Georg Schwarz, Langenfeld (DE); Klaus-Helmut Müller, Düsseldorf (DE); Dorothee Hoischen, Düsseldorf (DE); Mark Wilhelm Drewes, Langenfeld (DE); Peter Dahmen, Neuss (DE); Dieter Feucht, Monheim (DE); Rolf Pontzen, Leichlingen (DE); Akihiko Yanagi, Tochigi (JP); Shinichi Narabu, Ibaraki (JP); Toshio Goto, Tochigi (JP)

(73) Assignees: Bayer Aktiengesellschaft, Leverkusen (DE); Nihon Bayer Agrochem, K.K., Tokyo (JP)

( * ) Notice: Subject to any disclaimer, the term of this patent is extended or adjusted under 35 U.S.C. 154(b) by 8 days.

(21) Appl. No.: 10/181,327
(22) PCT Filed: Jan. 5, 2001
(86) PCT No.: PCT/EP01/00092
§ 371 (c)(1),
(2), (4) Date: Jul. 15, 2002
(87) PCT Pub. No.: WO01/53275
PCT Pub. Date: Jul. 26, 2001

(65) Prior Publication Data
US 2003/0153465 A1 Aug. 14, 2003

(30) Foreign Application Priority Data
Jan. 17, 2000 (DE) .......................................... 100 01 588
Aug. 14, 2000 (DE) .......................................... 100 39 723

(51) Int. Cl.$^7$ ...................... A01N 43/653; C07D 249/12
(52) U.S. Cl. ..................................... 504/273; 548/263.2
(58) Field of Search ........................ 504/273; 548/263.2

(56) References Cited

U.S. PATENT DOCUMENTS

| | | | |
|---|---|---|---|
| 4,780,127 A | 10/1988 | Michaely et al. | 71/103 |
| 4,806,146 A | 2/1989 | Carter | 71/98 |
| 4,816,066 A | 3/1989 | Michaely et al. | 71/123 |
| 4,946,981 A | 8/1990 | Carter et al. | 558/415 |
| 4,986,845 A | 1/1991 | Oya et al. | 71/92 |
| 5,006,158 A | 4/1991 | Carter et al. | 71/98 |
| 5,085,688 A | 2/1992 | Michaely et al. | 71/103 |
| 5,110,343 A | 5/1992 | Ueda et al. | 71/88 |
| RE34,779 E | 11/1994 | Oya et al. | 504/282 |
| 5,374,606 A | 12/1994 | Cramp et al. | 504/270 |
| 5,489,570 A | 2/1996 | Geach et al. | 504/261 |
| 5,650,533 A | 7/1997 | Roberts et al. | 560/17 |
| 5,656,573 A | 8/1997 | Roberts et al. | 504/271 |
| 5,747,424 A | 5/1998 | Roberts et al. | 504/271 |
| 5,804,532 A | 9/1998 | Cain et al. | 504/309 |
| 5,834,402 A | 11/1998 | Von Deyn et al. | 504/271 |
| 5,846,906 A | 12/1998 | von Deyn et al. | 504/221 |
| 5,859,283 A | 1/1999 | Cramp | 560/124 |
| 5,863,865 A | 1/1999 | Lee et al. | 504/271 |
| 5,948,917 A | 9/1999 | Adachi et al. | 548/247 |
| 6,004,903 A | 12/1999 | von Deyn et al. | 504/239 |
| 6,124,469 A | 9/2000 | Rheinheimer et al. | 548/240 |
| 6,153,759 A | 11/2000 | von Deyn et al. | 548/131 |
| 6,165,944 A | 12/2000 | von Deyn et al. | 504/271 |
| 6,297,198 B1 | 10/2001 | Lee | 504/271 |
| 2002/0025910 A1 | 2/2002 | Deyn et al. | 504/263 |

FOREIGN PATENT DOCUMENTS

| | | |
|---|---|---|
| CA | 2075348 | 2/1993 |
| CA | 1314557 | 3/1993 |
| EP | 03 525 43 | 1/1990 |
| EP | 06 097 97 | 8/1994 |
| EP | 07 411 28 | 11/1996 |
| WO | 92/19603 | 11/1992 |
| WO | 96/06094 | 2/1996 |
| WO | 96/11023 | 4/1996 |
| WO | 97/27187 | 7/1997 |
| WO | 97/41105 | 11/1997 |
| WO | 97/41116 | 11/1997 |
| WO | 97/41117 | 11/1997 |
| WO | 97/41118 | 11/1997 |
| WO | 97/45404 | 12/1997 |
| WO | 97/46530 | 12/1997 |
| WO | 98/28981 | 7/1998 |
| WO | 98/41089 | 9/1998 |
| WO | 99/03856 | 1/1999 |
| WO | 99/07688 | 2/1999 |
| WO | 99/10327 | 3/1999 |

(List continued on next page.)

OTHER PUBLICATIONS

Database Chemabs 'Online! Chemical Abstracts Service, Columbus, Ohio, US; Naohara, Kazuo et al: "Synergistic herbicides containing phenoxymethylpyrimidine derivatives" retrieved from STN Database accession No. 122: 3573 XP002166967 RNs 159596–12–0 to 159596–25–5 & JP 06 256113 A (Mitsubishi Petrochemical Co, Japan) Sep. 13, 1994.

(List continued on next page.)

*Primary Examiner*—Ceila Chang
*Assistant Examiner*—Sonya Wright
(74) *Attorney, Agent, or Firm*—Richard E. L. Henderson; Raymond J. Harmuth

(57) ABSTRACT

The invention relates to novel substituted aryl ketones of the general formula (I)

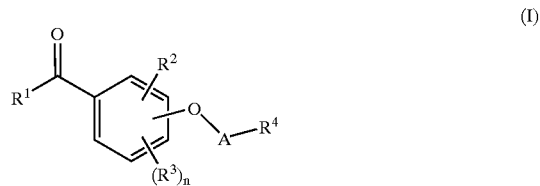

wherein all variables are as defined in the specification, and to processes for their preparation, to intermediates and to the use of these compounds as herbicides.

5 Claims, No Drawings

FOREIGN PATENT DOCUMENTS

| WO | 99/10328 | 3/1999 |
|---|---|---|
| WO | 99/41235 | 8/1999 |
| WO | 99/43672 | 9/1999 |
| WO | 99/57101 | * 11/1999 |
| WO | 00/17194 | 3/2000 |
| WO | 00/58295 | 10/2000 |
| WO | 00/66120 | 11/2000 |
| WO | 00/75130 | 12/2000 |
| WO | 01/00206 | 1/2001 |
| WO | 01/14303 | 3/2001 |

OTHER PUBLICATIONS

Database Chemabs 'Online! Chemical Abstracts Service, Columbus, Ohio, US; Oonishi, Akira et al: "Silver halide photographic photosensitive material containing diffusion-resistant dyes" retrieved from STN Database accession No. 121:311734 XP002166968 RN 159292–03–2 & JP 06 011797 A (Konishiroku Photo Ind, Japan) Jan. 21, 1994.

Database Chemabs 'Online! Chemical Abstracts Service, Columbus, Ohio, US; Daines, Robert A, et al: "Trisubstituted pyridine leukotriene B4 receptor antagonists: synthesis and structure–activity relationships" retrieved from STN Database accession No. 120: 77146 XP002166969 RN 152090–96–5 & J. Med. Chem. (1993), 36(22), 3321–32.

Database Chemabs 'Online! Chemical Abstracts Service, Columbus, Ohio, US; Wada, Nobuhide et al: "Preparation of 2–phenoxypyrimidines as herbicides" retrieved from STN Database accession No. 110: 192853 XP002166970 RN 120259–53–2 & JP 63 258463 A (Kumiai Chemical Industry Co., Ltd., Japan; Ihara Chemical Industry Co.,) Oct. 25, 1988.

Database Chemabs 'Online! Chemical Abstracts Service, Columbus, Ohio, US; Maynard, George D. et al: "Synthesis and structure–activity relationship of 4-(1H–benzimidazole-2–carbonyl)piperidines with dual histamine H1/tachykinin NK1 receptor antagonist activity" retrieved from STN Database accession No. 128:75364 XP002166965 RN 178372–23–1 & Bioorg. Med. Chem. Lett. (1997), 7(22), 2819–2824.

Database Chemabs 'Online! Chemical Abstracts Service, Columbus, Ohio, US; Walton, Paul H. et al: "Stereognostic coordination 4. The design and synthesis of a selective uranyl ion complexant" retrieved from STN Database accession No. 124:248683 XP002166966 RN 174909–17–2 & Inorg. Chim. Acta (1995), 240(1–2), 593–601.

Database Chemabs 'Online! Chemical Abstracts Service, Columbus, Ohio, US; Morita, Takeshi et al: "Cyclohexanediones and herbicides containing them" retrieved from STN Database accession No. 123:278720 XP002167114 RNs 169555–25–3, 169555–26–4, 169555–27–5, 169555–37–7, 169555–38–8, 169555–39–9 & JP 07 206808 A (Hokko Chem Ind Co, Japan) Aug. 8, 1995.

Database Chemabs 'Online! Chemical Abstracts Service, Columbus, Ohio, US; Fattakhov, S. G. et al: "Synthesis and transformations of 1, 3–bis' .omega. –(2– formylphenoxy-)alkyll– 6–methyluracils" retrieved from STN Database accession No. 133:335208 XP00216692 RN 304022–17–1 & Russ. J. Gen. Chem. (2000), 70(3), 461–468.

Database Chemabs 'Online! Chemical Abstracts Service, Columbus, Ohio, US; Grabowska, Urszula et al: "5–(Hydroxymethyl)oxazoles: Versatile Scaffolds for Combinatorial Solid–Phase Synthesis of 5–Substituted Oxazoles" retrieved from STN Database accession No. 133:222636 XP002166963 RN 291776–68–6 & J. Comb. Chem. (2000), 2(5), 475–490.

Database Chemabs 'Online! Chemical Abstracts Service, Columbus, Ohio, US; Vaz, Roy J. et al: "Use of CoMFA in validating the conformation used in designing 4–(1H–benzimidazole–2–carbonyl)piperidines with H1/NK1 receptor antagonist activity" retrieved from STN Database accession No. 128: 110371 XP002166964 RN 201595–84–8 & Bioorg. Med. Chem. Lett. (1997), 7(22), 2825–2830.

Database Chemabs 'Online! Chemical Abstracts Service, Columbus, Ohio, US; Morita, Takeshi et al: "Preparation of 2–'3–(1,3–dioxolan–4–ylmethoxy) benzoyll–1,3–cyclohexanedione derivatives as herbicides" retrieved from STN Database accession No. 122:155301 XP002166959 see list of RNs 161367–41–5 to 161367–61–9 Zusammenfassung & JP 06 321932 A (Hokko Chem Ind Co, Japan) Nov. 22, 1994.

Database Chemabs 'Online! Chemical Abstracts Service, Columbus, Ohio, US; Morita, Takeshi et al: "Preparation of dioxane and dioxolane derivatives as herbicides" retrieved from STN Database accession No. 122:160651 XP002166960 see list of RNs 161183–71–7 to 1651183–94–4 Zusammenfassung & JP 06 271562 A (Hokko Chem Ind Co, Japan) Sep. 27, 1994.

Database Chemabs 'Online! Chemical Abstracts Service, Columbus, Ohio, US; Someya, Shinzo et al: "Pyrazole derivatives as herbicides and process of their preparation" retrieved from STN Database accession No. 110:173224 XP002166961 RN 120003–13–6 Zusammenfassung & JP 63 264584 A (Agro–Kanesho Co., Ltd., Japan; Tosoh Corp.) Nov. 1, 1988.

* cited by examiner

SUBSTITUTED ARYL KETONES

The invention relates to novel substituted aryl ketones, to processes for their preparation and to their use as herbicides.

It is already known that certain substituted aryl ketones have herbicidal properties (cf. EP-A-090262, EP-A-135191, EP-A-186118, EP-A-186119, EP-A-186120, EP-A-319075, EP-A-352543, EP-A-418175, EP-A-487357, EP-A-527036, EP-A-527037, EP-A-560483, EP-A-609797, EP-A-609798, EP-A-625505, EP-A-625508, EP-A-636622, U.S. Pat. No. 5,804,532, U.S. Pat. No. 5,834,402, U.S. Pat. No. 5,846,906, U.S. Pat. No. 5,863,865, WO-A-96/26192, WO-A-96/26193, WO-A-96/26200, WO-A-96/26206, WO-A-97/27187, WO-A-97/35850, WO-A-97/41105, WO-A-97/41116, WO-A-97/41117, WO-A-97/41118, WO-A-97/43270, WO-A-97/46530, WO-A-98/28981, WO-A-98/31681, WO-A-98/31682, WO-A-99/03856, WO-A-99/07688, WO-A-99/10327, WO-A-99/10328). However, the activity of these compounds is not entirely satisfactory.

This invention, accordingly, provides the novel substituted aryl ketones of the general formula (I)

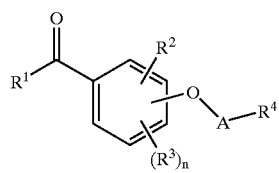

(I)

in which n represents the number 0, 1 or 2,

A represents alkanediyl (alkylene), $R^1$ represents one of the groupings below

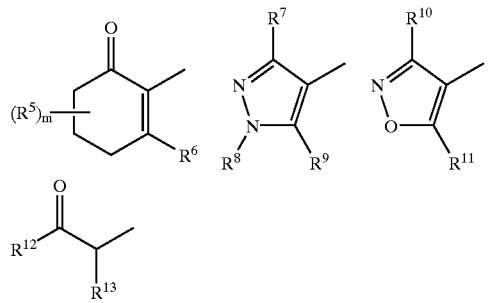

where m represents the numbers 0 to 6, $R^5$ represents halogen or represents in each case optionally substituted alkyl, alkylthio or aryl or—if m represents 2—optionally also together with a second radical $R^5$ represents alkanediyl (alkylene), $R^6$ represents hydroxyl, formyloxy, halogen, or represents in each case optionally substituted alkoxy, alkylthio, alkylsulphinyl, alkylsulphonyl, alkylcarbonyloxy, alkoxycarbonyloxy, alkylaminocarbonyloxy, alkylsulphonyloxy, alkenyloxy, alkinyloxy, aryloxy, arylthio, arylsulphinyl, arylsulphonyl, arylcarbonyloxy, arylcarbonylalkoxy, arylsulphonyloxy, arylalkoxy, arylalkylthio, arylalkylsulphinyl or arylalkylsulphonyl, $R^7$ represents hydrogen, cyano, carbamoyl, thiocarbamoyl, halogen, or represents in each case optionally substituted alkyl, alkoxy, alkylthio, alkylsulphinyl, alkylsulphonyl, alkoxycarbonyl or cycloalkyl, $R^8$ represents hydrogen or represents in each case optionally substituted alkyl, alkenyl, alkinyl, cycloalkyl, cycloalkylalkyl, aryl or arylalkyl, $R^9$ represents hydroxyl, formyloxy, or represents in each case optionally substituted alkoxy, alkylcarbonyloxy, alkoxycarbonyloxy, alkylaminocarbonyloxy, alkylsulphonyloxy, alkenyloxy, alkinyloxy, arylalkoxy, arylcarbonyloxy, arylcarbonylalkoxy or arylsulphonyloxy, $R^{10}$ represents hydrogen, cyano, carbamoyl, thiocarbamoyl, halogen, or represents in each case optionally substituted alkyl, alkylcarbonyl, alkoxy, alkoxycarbonyl, alkylthio, alkylsulphinyl or alkylsulphonyl, $R^{11}$ represents hydrogen or represents in each case optionally substituted alkyl or cycloalkyl, $R^{12}$ represents hydrogen or represents in each case optionally substituted alkyl or cycloalkyl, and $R^{13}$ represents hydrogen, cyano, carbamoyl, halogen, or represents in each case optionally substituted alkyl, alkoxy, alkoxycarbonyl, alkylthio, alkylsulphinyl or alkylsulphonyl, $R^2$ represents hydrogen, nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino or dialkylaminosulphonyl, $R^3$ represents nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino or dialkylaminosulphonyl, and $R^4$ represents an optionally substituted 4- to 12-membered, saturated or unsaturated, monocyclic or bicyclic heterocyclic grouping which contains 1 to 4 hetero atoms (up to 4 nitrogen atoms and optionally—alternatively, or additionally—one or two oxygen atoms or one or two sulphur atoms, or one or two SO groupings or one or two $SO_2$ groupings), and which additionally contains one to three oxo groups (C=O) and/or thioxo groups (C=S) as components of the heterocycle, including all possible tautomeric forms of the compounds of the general formula (I) and the possible salts and acid or base adducts of the compounds of the general formula (I)-.

In the definitions, the hydrocarbon chains, such as alkyl or alkanediyl, are in each case straight-chain or branched—including in combination with heteroatoms, such as in alkoxy.

The compounds of the general formula (I) according to the invention may contain one or more asymmetrically substituted carbon atoms, and they may therefore be present in different enantiomeric (R- and S-configured forms) or diastereomeric forms. The invention relates both to the various possible individual enantiomeric or stereoisomeric forms of the compounds of the general formula (I) and to the mixtures of these stereoisomeric compounds.

Preferred substituents or preferred ranges of the radicals present in the formulae listed above and below are defined below.

n preferably represents the number 0 or 1.

m preferably represents the number 0, 1, 2, 3 or 4.

A preferably represents alkanediyl (alkylene) having 1 to 6 carbon atoms.

$R^1$ preferably represents one of the groupings below

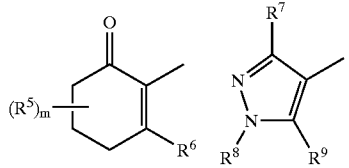

$R^2$ preferably represents hydrogen, nitro, cyano, carboxyl, carbamoyl, thiocarbamoyl, halogen, or represents in each case optionally cyano-, halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkoxy, alkylthio, alkylsulphinyl, alkylsulphonyl, alkylamino, dialkylamino or dialkylaminosulphonyl having in each case 1 to 6 carbon atoms in the alkyl groups.

$R^3$ preferably represents nitro, cyano, carboxyl, carbamoyl, thiocarbamoyl, halogen, or represents in each case optionally cyano, halogen, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkoxy, alkylthio, alkylsulphinyl, alkylsulphonyl, alkylamino, dialkylamino or dialkylaminosulphonyl having in each case 1 to 6 carbon atoms in the alkyl groups.

$R^4$ preferably represents one of the heterocyclic groupings below

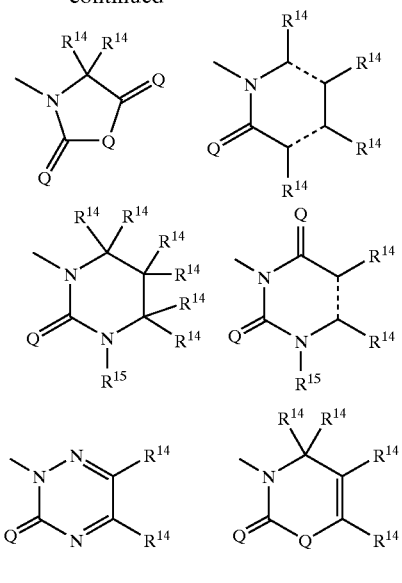

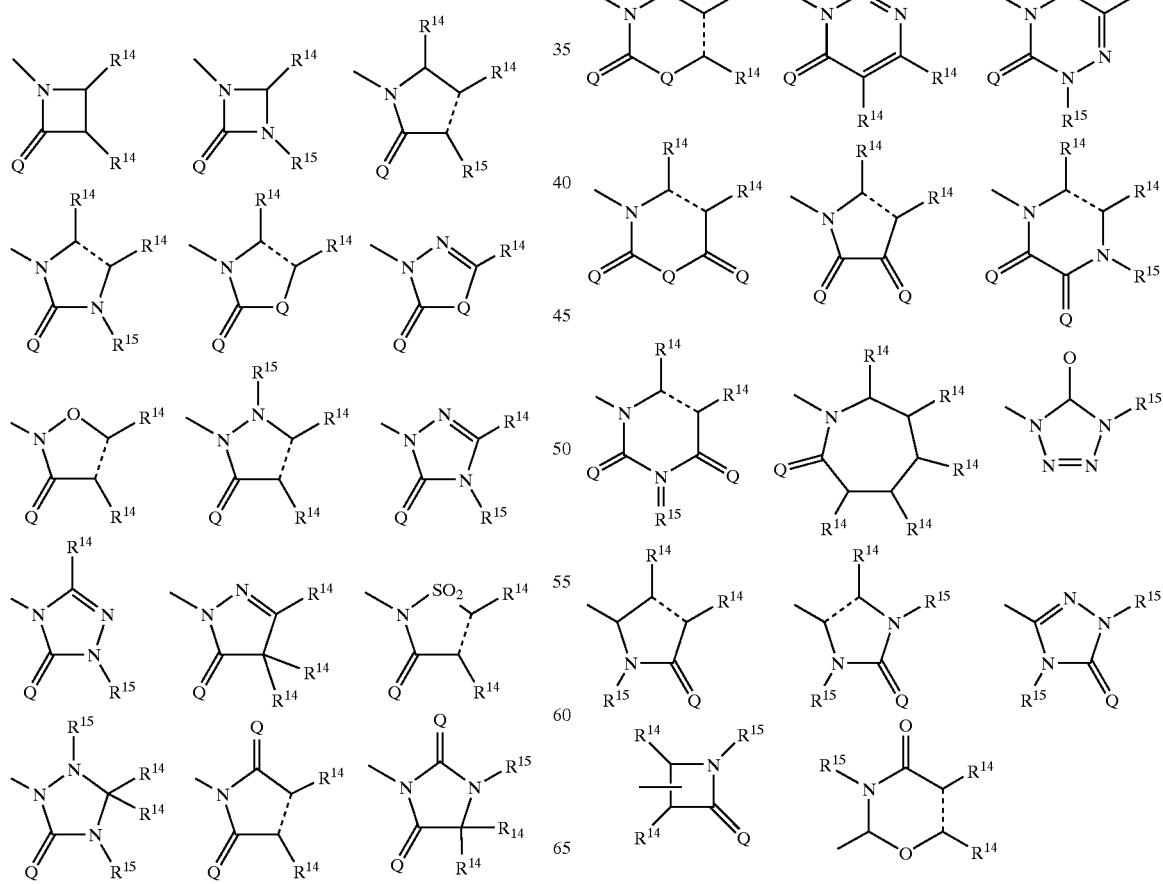

where in each case the broken bond is a single bond or a double bond.

Q represents oxygen or sulphur, $R^{14}$ represents hydrogen, hydroxyl, mercapto, cyano, halogen, represents in each case optionally cyano-, halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkylcarbonyl, alkoxy, alkoxycarbonyl, alkylthio, alkylsulphinyl or alkylsulphonyl having in each case up to 6 carbon atoms in the alkyl groups, represents in each case optionally halogen-substituted alkylamino or dialkylamino having in each case up to 6 carbon atoms in the alkyl groups, represents in each case optionally halogen-substituted alkenyl, alkinyl, alkenyloxy, alkenylthio or alkenylamino having in each case up to 6 carbon atoms in the alkenyl or alkinyl groups, represents in each case optionally halogen-substituted cycloalkyl, cycloalkyloxy, cycloalkylthio, cycloalkylamino, cycloalkylalkyl, cycloalkylalkoxy, cycloalkylalkylthio or cycloalkylalkylamino having in each case 3 to 6 carbon atoms in the cycloalkyl groups and optionally up to 4 carbon atoms in the alkyl moiety, or represents in each case optionally halogen-, $C_1$–$C_4$-alkyl- or $C_1$–$C_4$-alkoxy-substituted phenyl, phenyloxy, phenylthio, phenylamino, benzyl, benzyloxy, benzylthio or benzylamino, represents pyrrolidino, piperidino or morpholino, or—if two adjacent radicals $R^{14}$ and $R^{14}$ are located at a double bond—also together with the adjacent radical $R^{14}$ represents a benzo grouping, and $R^{15}$ represents hydrogen, hydroxyl, amino, alkylideneamino having up to 4 carbon atoms, represents in each case optionally halogen- or $C_1$–$C_4$-alkoxy-substituted alkyl, alkoxy, alkylamino, dialkylamino or alkanoylamino having in each case up to 6 carbon atoms in the alkyl groups, represents in each case optionally halogen-substituted alkenyl, alkinyl or alkenyloxy having in each case up to 6 carbon atoms in the alkenyl or alkinyl groups, represents in each case optionally halogen-substituted cycloalkyl, cycloalkylalkyl or cycloalkylamino having in each case 3 to 6 carbon atoms in the cycloalkyl groups and optionally up to 3 carbon atoms in the alkyl moiety, or represents in each case optionally halogen-, $C_1$–$C_4$-alkyl- or $C_1$–$C_4$-alkoxy-substituted phenyl or benzyl, or together with an adjacent radical $R^{14}$ or $R^{15}$ represents optionally halogen- or $C_1$–$C_4$-alkyl-substituted alkanediyl having 3 to 5 carbon atoms, where the individual radicals $R^{14}$ and $R^{15}$—if more than one of them are attached to the same heterocyclic groupings—can have identical or different meanings within the scope of the above definition.

$R^5$ preferably represents halogen, represents in each case optionally cyano-, halogen- or $C_1$–$C_4$-alkoxy-substituted alkyl or alkylthio having in each case 1 to 6 carbon atoms, represents optionally halogen-, $C_1$–$C_4$-alkyl- or $C_1$–$C_4$-alkoxy-substituted phenyl, or optionally also—if m represents 2—together with a second radical $R^5$ represents alkanediyl (alkylene) having 2 to 6 carbon atoms.

$R^6$ preferably represents hydroxyl, formyloxy, or represents in each case optionally cyano-, halogen- or $C_1$–$C_4$-alkoxy-substituted alkoxy, alkylthio, alkylsulphinyl, alkylsulphonyl, alkylcarbonyloxy, alkoxycarbonyloxy-, alkylaminocarbonyloxy or alkylsulphonyloxy having in each case 1 to 6 carbon atoms in the alkyl groups, represents in each case optionally cyano- or halogen-substituted alkenyloxy or alkinyloxy having in each case 2 to 6 carbon atoms, or represents in each case optionally nitro-, cyano-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted aryloxy, arylthio, arylsulphinyl, arylsulphonyl, arylcarbonyloxy, arylcarbonylalkoxy, arylsulphonyloxy, arylalkoxy, arylalkylthio, arylalkylsulphinyl or arylalkylsulphonyl having in each case 6 or 10 carbon atoms in the aryl group and optionally 1 to 4 carbon atoms in the alkyl moiety.

$R^7$ preferably represents hydrogen, cyano, carbamoyl, thiocarbamoyl, halogen, represents in each case optionally cyano-, halogen- or $C_1$–$C_4$-alkoxy-substituted alkyl, alkoxy, alkylthio, alkylsulphinyl, alkylsulphonyl or alkoxycarbonyl having in each case 1 to 6 carbon atoms in the alkyl groups, or represents optionally cyano-, halogen- or $C_1$–$C_4$-alkyl-substituted cycloalkyl having 3 to 6 carbon atoms.

$R^8$ preferably represents hydrogen, represents in each case optionally cyano-, halogen- or $C_1$–$C_4$-alkoxy-substituted alkyl having 1 to 6 carbon atoms, represents in each case optionally cyano- or halogen-substituted alkenyl or alkinyl having in each case 2 to 6 carbon atoms, represents in each case optionally cyano-, halogen- or $C_1$–$C_4$-alkyl-substituted cycloalkyl or cycloalkylalkyl having in each case 3 to 6 carbon atoms in the cycloalkyl group and optionally 1 to 4 carbon atoms in the alkyl moiety, or represents in each case optionally nitro-, cyano-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted aryl or arylalkyl having in each case 6 or 10 carbon atoms in the aryl group and optionally 1 to 4 carbon atoms in the alkyl moiety.

$R^9$ preferably represents hydroxyl, formyloxy, represents in each case optionally cyano-, halogen- or $C_1$–$C_4$-alkoxy-substituted alkoxy, alkylcarbonyloxy, alkoxycarbonyloxy, alkylaminocarbonyloxy or alkylsulphonyloxy having in each case 1 to 6 carbon atoms in the alkyl groups, represents in each case optionally cyano- or halogen-substituted alkenyloxy or alkinyloxy having in each case 2 to 6 carbon atoms, or represents in each case optionally nitro-, cyano-, halogen-, $C_1$–$C_4$-alkyl-, $C_1$–$C_4$-halogenoalkyl-, $C_1$–$C_4$-alkoxy- or $C_1$–$C_4$-halogeno-alkoxy-substituted arylalkoxy, arylcarbonyloxy, arylcarbonylalkoxy or arylsulphonyloxy having in each case 6 or 10 carbon atoms in the aryl group and optionally 1 to 4 carbon atoms in the alkyl moiety.

$R^{10}$ preferably represents hydrogen, cyano, carbamoyl, thiocarbamoyl, halogen, or represents in each case optionally cyano-, halogen- or $C_1$–$C_4$-alkoxy-substituted alkyl, alkylcarbonyl, alkoxy, alkoxycarbonyl, alkylthio, alkylsulphinyl or alkylsulphonyl having in each case 1 to 6 carbon atoms in the alkyl groups.

$R^{11}$ preferably represents hydrogen, represents optionally cyano-, halogen- or $C_1$–$C_4$-alkoxy-substituted alkyl having 1 to 6 carbon atoms or represents optionally cyano-, halogen- or $C_1$–$C_4$-alkyl-substituted cycloalkyl having 3 to 6 carbon atoms.

$R^{12}$ preferably represents hydrogen, represents optionally cyano-, halogen- or $C_1$–$C_4$-alkoxy-substituted alkyl having 1 to 6 carbon atoms or represents optionally cyano-, halogen- or $C_1$–$C_4$-alkyl-substituted cycloalkyl having 3 to 6 carbon atoms.

$R^{13}$ preferably represents hydrogen, cyano, carbamoyl, halogen, or represents in each case optionally cyano-, halogen- or $C_1$–$C_4$-alkoxy-substituted alkyl, alkoxy, alkoxycarbonyl, alkylthio, alkylsulphinyl or alkylsulphonyl having in each case 1 to 6 carbon atoms in the alkyl groups.

m particularly preferably represents the numbers 0, 1, 2 or 3.

A particularly preferably represents methylene, ethane-1,2-diyl (dimethylene), ethane-1,1-diyl, propane-1,2-diyl, propane-1,3-diyl (trimethylene), butane-1,2-diyl, butane-1,3-diyl or butane-1,4-diyl (tetramethylene).

$R^2$ particularly preferably represents hydrogen, nitro, cyano, carboxyl, carbamoyl, thiocarbamoyl, fluorine, chlorine-, bromine, iodine, or represents in each case optionally fluorine- and/or chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, represents in each case optionally fluorine- and/or chlorine-, methoxy-ethoxy-, n- or i-propoxy-substituted methoxy, ethoxy, n- or i-propoxy, represents in each case optionally fluorine- and/or chlorine-substituted methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents methylamino, ethylamino, n- or i-propylamino, dimethylamino, diethylamino, dimethylaminosulphonyl or diethylaminosulphonyl.

$R^3$ particularly preferably represents nitro, cyano, carboxyl, carbamoyl, thiocarbamoyl, fluorine, chlorine, bromine, represents in each case optionally fluorine- and/or chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, represents in each case optionally fluorine- and/or chlorine-, methoxy-, ethoxy-, n- or i-propoxy-substituted methoxy, ethoxy, n- or i-propoxy, represents in each case fluorine- and/or chorine-substituted methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents methylamino, ethylamino, n- or i-propylamino, dimethylamino, diethylamino, dimethylaminosulphonyl or diethylaminosulphonyl $R^4$ particularly preferably represents one of the heterocyclic groupings below.

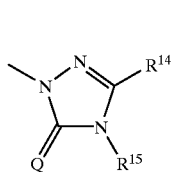
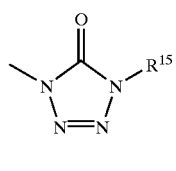
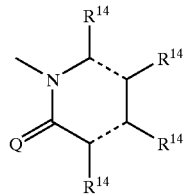

-continued

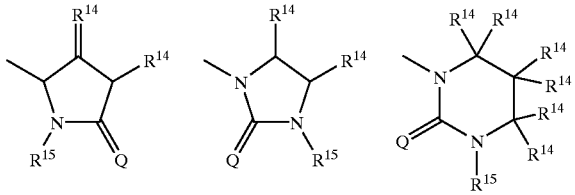

$R^5$ particularly preferably represents fluorine, chlorine, bromine, represents in each case optionally cyano-, fluorine-, chlorine-, methoxy- or ethoxy-substituted methyl, ethyl, n- or i-propyl, n-, i-, s- or t-butyl, methylthio, ethylthio, n- or i-propylthio, n-, i-, s- or t-butylthio, represents optionally fluorine-, chlorine-, methyl- or methoxy-substituted phenyl, or optionally also - if m represents 2—together with a second radical $R^5$ represents ethane-1,2-diyl (dimethylene), propane-1,3-diyl (trimethylene) or butane-1,4-diyl (tetramethylene).

$R^6$ particularly preferably represents hydroxyl, formyloxy, represents in each case optionally cyano-, fluorine-, chlorine-, methoxy- or ethoxy-substituted methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents in each case optionally cyano-, fluorine-, chlorine- or bromine-substituted propenyloxy, butenyloxy, propinyloxy or butinyloxy, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenoxy, phenylthio, phenylsulphinyl, phenylsulphonyl, benzoyloxy, benzoylmethoxy, phenylsulphonyloxy, phenylmethoxy, phenylmethylthio, phenylmethylsulphinyl or phenylmethylsulphonyl.

$R^7$ particularly preferably represents hydrogen, cyano, carbamoyl, thiocarbamoyl, fluorine, chlorine, bromine, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methoxycarbonyl, ethoxycarbonyl, n- or i-propoxycarbonyl, or represents in each case optionally cyano-, fluorine-, chlorine-, bromine-, methyl- or ethyl-substituted cyclopropyl, cyclobutyl, cyclopentyl or cyclohexyl.

$R^8$ particularly preferably represents hydrogen, represents in each case optionally cyano-, fluorine-, chlorine-, bromine-, methoxy- or ethoxy-substituted methyl, ethyl, n- or i-propyl, n-, i-, s- or t-butyl, represents in each case optionally cyano-, fluorine-, chlorine- or bromine-substituted propenyl, butenyl, propinyl or butinyl, represents in each case optionally cyano-, fluorine-, chlorine-, bromine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally nitro-, cyano-, fluorine-, chlorine-, bromine-, methyl-, ethyl-, n- or i-propyl, n-, i-, s- or t-butyl, trifluoromethyl, methoxy, ethoxy, n- or i-propoxy, n-, i-, s- or t-butoxy-, difluoromethoxy- or trifluoromethoxy-substituted phenyl or benzyl.

$R^9$ particularly preferably represents hydroxyl, formyloxy, represents in each case optionally cyano-, fluorine-, chlorine-, bromine-, methoxy-, ethoxy-, n- or i-propoxy-substituted methoxy, ethoxy, n- or i-propoxy, n-, i-, s- or t-butoxy, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents in each case optionally cyano-, fluorine-, chlorine- or bromine-substituted propenyloxy, butenyloxy, propinyloxy or butinyloxy, or represents in each case optionally nitro-, cyano-, fluorine-, chlorine-, bromine-, methyl-, ethyl-, n- or i-propyl-, propoxy-, n-, i-, s- or t-butoxy-, difluoromethoxy- or trifluoromethoxy-substituted phenylmethoxy, benzoyloxy, benzoylmethoxy or phenylsulphonyloxy.

$R^{10}$ particularly preferably represents hydrogen, cyano, carbamoyl, thiocarbamoyl, fluorine, chlorine, bromine, or represents in each case optionally cyano-, fluorine-, chlorine-, bromine-, methoxy-, ethoxy-, n- or i-propoxy-substituted methyl, ethyl, n- or i-propyl, n-, i-, s- or t-butyl, acetyl, propionyl, n- or i-butyroyl, methoxy, ethoxy, n- or i-propoxy, n-, i-, s- or t-butoxy, methoxycarbonyl, ethoxycarbonyl, n- or i-propoxycarbonyl, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl.

$R^{11}$ particularly preferably represents hydrogen, represents in each case optionally cyano-, fluorine-, chlorine-, bromine-, methoxy- or ethoxy-substituted methyl, ethyl, n- or i-propyl, n-, i-, s- or t-butyl, or represents in each case optionally cyano-, fluorine-, chlorine-, bromine-, methyl- or ethyl-substituted cyclopropyl, cyclobutyl, cyclopentyl or cyclohexyl.

$R^{12}$ particularly preferably represents hydrogen, represents in each case optionally cyano-, fluorine-, chlorine-, bromine-, methoxy- or ethoxy-substituted methyl, ethyl, n- or i-propyl, n-, i-, s- or t-butyl, or represents in each case optionally cyano-, fluorine-, chlorine-, bromine-, methyl- or ethyl-substituted cyclopropyl, cyclobutyl, cyclopentyl or cyclohexyl.

$R^{13}$ particularly preferably represents hydrogen, cyano, carbamoyl, fluorine, chlorine, bromine, or represents in each case optionally cyano-, fluorine-, chlorine-, bromine-, methoxy- or ethoxy-substituted methyl, ethyl, n- or i-propyl, n-, i-, s- or t-butyl, methoxy, ethoxy, n- or i-propoxy, n-, i-, s- or t-butoxy, methoxycarbonyl, ethoxycarbonyl, n- or i-propoxycarbonyl, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl.

$R^{14}$ particularly preferably represents hydrogen, hydroxyl, mercapto, cyano, fluorine, chlorine, bromine, iodine, represents in each case optionally fluorine-, chlorine-, methoxy-, ethoxy-, n- or i-propoxy-, n-, i-, s- or t-butoxy-, methylthio-, ethylthio-, n- or i-propylthio-, n-, i-, s- or t-butylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, represents methylamino, ethylamino, n- or i-propylamino, n-, i-, s- or t-butylamino, dimethylamino, diethylamino, di-n-propylamino or di-i-propylamino, represents in each case optionally fluorine- and/or chlorine-substituted ethenyl, propenyl, butenyl, ethinyl, propinyl, butinyl, propenyloxy, butenyloxy, propenylthio, butenylthio, propenylamino or butenylamino, represents in each case optionally fluorine- and/or chlorine-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or represents in each case optionally fluorine-, chlorine-, methyl-, ethyl-, n- or i-propyl-, n-, i-, s- or t-butyl-, methoxy-, ethoxy-, n- or i-propoxy-substituted phenyl, phenyloxy, phenylthio, phenylamino, benzyl, benzyloxy, benzylthio or benzylamino, represents pyrrolidino, piperidino or morpholino, or—if two adjacent radicals $R^{14}$ and $R^{14}$ are located at a double bond—together with the adjacent radical $R^{14}$ also represents a benzo grouping.

$R^{15}$ particularly preferably represents hydrogen, hydroxyl, amino, represents in each case optionally fluorine- and/or chlorine-, methoxy- or ethoxy-substituted methyl, ethyl, n- or i- or s-butyl, methoxy, ethoxy, n- or i-propoxy, methylamino, ethylamino or dimethylamino, represents in each case optionally fluorine- and/or chlorine-substituted ethenyl, propenyl, ethinyl, propinyl or propenyloxy, represents in each case optionally fluorine- and/or chlorine-substituted cyclopropyl, cyclobutyl, cyclopentyl, cyclohexyl, cyclopropylmethyl, cyclobutylmethyl, cyclopentylmethyl, cyclohexylmethyl, or represents in each case optionally fluorine-, chlorine-, methyl-, ethyl-, n- or i-propyl-, n-, i-, s- or t-butyl-, methoxy-, ethoxy-, n- or i-propoxy-substituted phenyl or benzyl, or together with an adjacent radical $R^{14}$ or $R^{15}$ represents in each case optionally methyl- and/or ethyl-substituted propane-1,3-diyl (trimethylene) or butane-1,4-diyl (tetramethylene).

A very particularly preferably represents methylene or dimethylene.

m very particularly preferably represents the number 0, 1 or 2, $R^2$ very particularly preferably represents hydrogen, nitro, cyano, fluorine, chlorine, bromine, iodine, methyl, ethyl, difluoromethyl, trifluoromethyl, dichloromethyl, trichloromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl.

$R^3$ very particularly preferably represents nitro, cyano, fluorine, chlorine, bromine, iodine, methyl, ethyl, difluoromethyl, trifluoromethyl, dichloromethyl, trichloromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl.

$R^5$ very particularly preferably represents in each case optionally fluorine- or chlorine-substituted methyl, ethyl, n- or i-propyl, methylthio, ethylthio, n- or i-propylthio, represents phenyl, or optionally also—if m represents 2—together with a second radical $R^5$ represents ethane-1,2-diyl (dimethylene), propane-1,3-diyl (trimethylene) or butane-1,4-diyl (tetramethylene).

$R^6$ very particularly preferably represents hydroxyl, formyloxy, represents in each case optionally fluorine-, chlorine-, methoxy- or ethoxy-substituted methoxy, ethoxy, n- or i-propoxy, methylthio, ethylthio, n- or i-propylthio, methylsulphinyl, ethylsulphinyl, methylsulphonyl, ethylsulphonyl, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents propenyloxy or propinyloxy, or represents in each case optionally nitro-, cyano-, fluorine-, chlorine-, bromine-, methyl-, ethyl-, n- or i-propyl-, trifluoromethyl-, methoxy-, ethoxy-, n- or i-propoxy-, difluoromethoxy- or trifluoromethoxy-substituted phenoxy, phenylthio, phenylsulphinyl, phenylsulphonyl, benzoyloxy, benzoylmethoxy, phenylsulphonyloxy, phenylmethoxy, phenylmethylthio, phenylmethylsulphinyl or phenylmethylsulphonyl.

$R^7$ very particularly preferably represents hydrogen, cyano, fluorine, chlorine, bromine, represents in each case optionally fluorine-, chlorine-, methoxy- or ethoxy-substituted methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, methoxycarbonyl, ethoxycarbonyl, n- or i-propoxycarbonyl.

$R^8$ very particularly preferably represents hydrogen, represents in each case optionally cyano-, fluorine-, chlorine-, methoxy- or ethoxy-substituted methyl, ethyl, n- or i-propyl, represents in each case optionally fluorine- or chlorine-substituted propenyl or propinyl, represents optionally fluorine-, chlorine-, bromine-, methyl- or ethyl-substituted cyclopropyl, or represents in each case optionally fluorine-, chlorine-, bromine-, methyl-, ethyl-, n- or i-propyl-, trifluoromethyl-, methoxy-, ethoxy-, n- or i-propoxy-, difluoromethoxy- or trifluoromethoxy-substituted phenyl or benzyl.

$R^9$ very particularly preferably represents hydroxyl, formyloxy, represents in each case optionally cyano-, fluorine-, chlorine-, bromine-, methoxy-, ethoxy-, n- or i-propoxy-substituted methoxy, ethoxy, n- or i-propoxy, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents propenyloxy or propinyloxy, or represents in each case optionally nitro-, cyano-, fluorine-, chlorine-, bromine-, methyl-, ethyl-, n- or i-propyl-, trifluoromethyl-, methoxy-, ethoxy-, n- or i-propoxy-, difluoromethoxy- or trifluoromethoxy-substituted phenylmethoxy, benzoyloxy, benzoylmethoxy or phenylsulphonyloxy.

$R^{10}$ very particularly preferably represents hydrogen, cyano, fluorine, chlorine, bromine, or represents in each case optionally fluorine-, chlorine-, methoxy-, ethoxy-, n- or i-propoxy-substituted methyl, ethyl, n- or i-propyl, acetyl, propionyl, n- or i-butyroyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl or ethylsulphonyl.

$R^{11}$ very particularly preferably represents hydrogen, represents in each case optionally fluorine-, chlorine-, bromine-, methoxy- or ethoxy-substituted methyl, ethyl, n- or i-propyl, or represents in each case optionally fluorine-, chlorine-, bromine-, methyl- or ethyl-substituted cyclopropyl.

$R^{12}$ very particularly preferably represents hydrogen, represents in each case optionally fluorine-, chlorine-, methoxy- or ethoxy-substituted methyl, ethyl, n- or i-propyl, or represents in each case optionally fluorine-, chlorine-, bromine-, methyl- or ethyl-substituted cyclopropyl.

$R^{13}$ very particularly preferably represents hydrogen, cyano, fluorine, chlorine, bromine, or represents in each case optionally fluorine-, chlorine-, bromine-, methoxy- or ethoxy-substituted methyl, ethyl, n- or i-propyl, methoxy, ethoxy, or n- or i-propoxy, methoxycarbonyl, ethoxycarbonyl, n- or i-propoxycarbonyl, methylthio, ethylthio, n- or i-propylthio, methylsulphinyl, ethylsulphinyl, n- or i-propylsulphinyl, methylsulphonyl, ethylsulphonyl, n- or i-propylsulphonyl.

$R^{14}$ very particularly preferably represents hydrogen, hydroxyl, mercapto, cyano, fluorine, chlorine, bromine, iodine, represents in each case optionally fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, represents methylamino, ethylamino, n- or i-propylamino, dimethylamino or diethylamino, represents in each case optionally fluorine- and/or chlorine-substituted ethenyl, propenyl, ethinyl, propinyl, propenyloxy, propenylthio or propenylamino, represents in each case optionally fluorine- and/or chlorine-substituted cyclopropyl, cyclopropyloxy, cyclopropylamino, cyclopropylmethyl, cyclopropylmethoxy or cyclopropylmethylamino, or represents in each case optionally fluorine-, chlorine-, methyl-, ethyl-, n- or i-propyl-, methoxy-, ethoxy-, n- or i-propoxy-substituted phenyl, phenyloxy, phenylthio, phenylamino, benzyl, benzyloxy, benzylthio or benzylamino, or—if two adjacent radicals $R^{14}$ and $R^{14}$ are located at a double bond—together with the adjacent radical $R^{14}$ also represents a benzo grouping.

$R^{15}$ very particularly preferably represents hydrogen, hydroxyl, amino, represents in each case optionally fluorine- and/or chlorine-, methoxy- or ethoxy-substituted methyl, ethyl, n- or i-propyl, methoxy, ethoxy, n- or i-propoxy, methylamino, ethylamino or dimethylamino, represents propenyl or propinyl, represents in each case optionally fluorine- and/or chlorine-substituted cyclopropyl, cyclobutyl or cyclopropylmethyl, or represents in each case optionally fluorine-, chlorine-, methyl-, ethyl-, n- or i-propyl-, methoxy-, ethoxy-, n- or i-propoxy-substituted phenyl or benzyl, or together with an adjacent radical $R^{14}$ or $R^{15}$ represents in each case optionally methyl- and/or ethyl-substituted propane-1,3-diyl (trimethylene) or butane-1,4-diyl (tetramethylene).

Preference according to the invention is given to the compounds of the formula (I) which contain a combination of the meanings listed above as being preferred.

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Particular emphasis is given to the compounds of the general formulae (I-1) to (I-3):

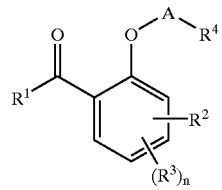

(I-1)

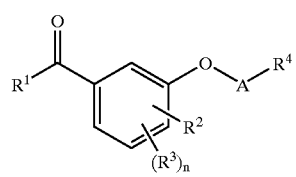

(I-2)

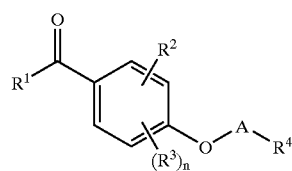

(I-3)

Here, n, A, $R^1$, $R^2$, $R^3$ and $R^4$ in each case have the most preferred meaning.

Very particular emphasis is given to the compounds of the general formulae (I-2A) to (I-2D):

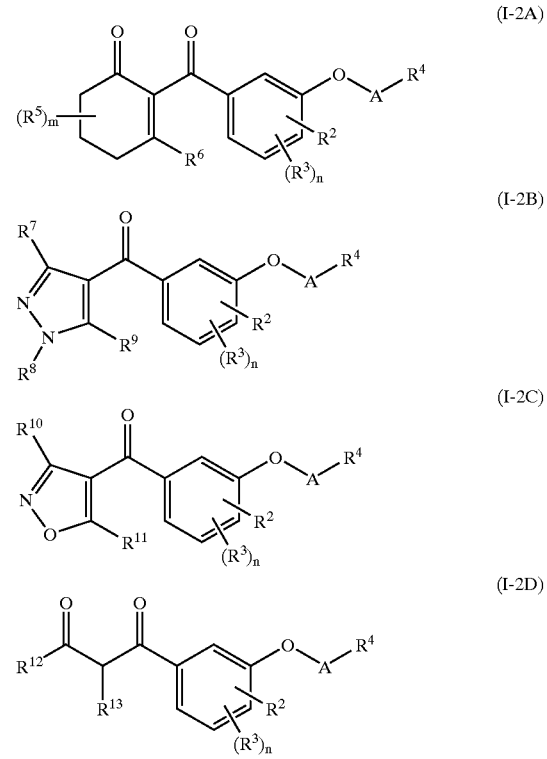

Here, m, n, A, $R^2$, $R^3$, $R^4$, $R^5$, $R^6$, $R^7$, $R^8$, $R^9$, $R^{10}$, $R^{11}$, $R^{12}$ and $R^{13}$ in each case have the most preferred meaning.

The invention also provides the sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium and di-($C_1$–$C_2$-alkyl)-benzyl-ammonium salts of compounds of the formula (I) in which preferably n, A, $R^1$, $R^2$, $R^3$ and $R^4$ have the meanings given above as being preferred, particularly preferred or very particularly preferred.

The general or preferred radical definitions given above apply both to the end products of the formula (I) and, correspondingly, to the starting materials or intermediates required in each case for the preparation. These radical definitions can be combined with one another as desired, i.e. including combinations between the given preferred ranges.

The novel substituted aryl ketones of the general formula (I) have strong and selective herbicidal activity.

the novel substituted aryl ketones of the general formula (I) are obtained when (a) substituted benzoic acids of the general formula (II)

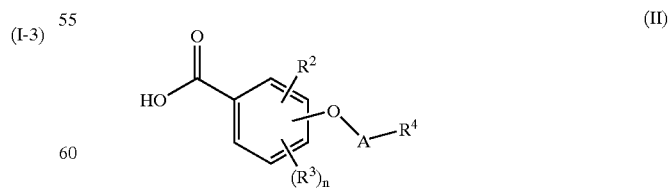

(II)

in which n, A, $R^2$, $R^3$ and $R^4$ are each as defined above, or reactive derivatives thereof, such as, for example, the corresponding acid halides, acid cyanides or esters are reacted with compounds of the general formula (III)

$$R^1—H \quad (III)$$

in which

R¹ is as defined above, if appropriate in the presence of a dehydrating agent, if appropriate in the presence of one or more reaction auxiliaries and if appropriate in the presence of a diluent, or where (b) substituted benzoyl ketones of the general formula (Ia)

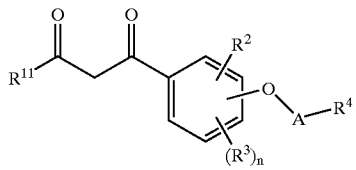

in which n, A, R², R³, R⁴ and R¹¹ are each as defined above, are reacted with an orthoformic ester or a N,N-dimethylformamide acetal or with a cyanoformic ester or with carbon disulphide and an alkylating agent, and then with hydroxylamine or an acid adduct thereof, if appropriate in the presence of one or more reaction auxiliaries and if appropriate in the presence of one or more diluents, and, if appropriate, following the practice of the process (a) or (b) according to the invention, the resulting compounds of the general formula (I) are subjected in a customary manner to substitution, oxidation or reduction reactions within the scope of the definition of the substituents and/or the compounds of the general formula (I) are converted in a customary manner into salt-like compounds.

Using, for example, 4-chloro-3-[(3,4-dimethyl-5-oxo-4,5-dihydro-1H-1,2,4-triazol-3-yl)-methoxy]-2-fluoro-benzoic acid and 1,3-dimethyl-5-hydroxy-pyrazole as starting materials, the course of the reaction in the process (a) according to the invention can be illustrated by the following equation:

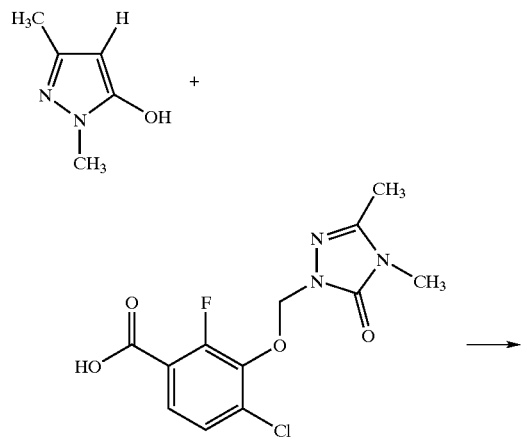

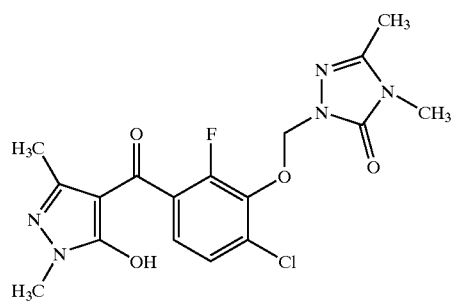

Using, for example, 1-[2-chloro-4-methyl-3-[2-(2-oxo-1 (2H)-pyridinyl)-ethoxy]-phenyl]-3-cyclopropyl-1,3-propanedione, ethyl cyanoformate and hydroxylamine as starting materials, the course of the reaction in the process (b) according to the invention can be illustrated by the following equation:

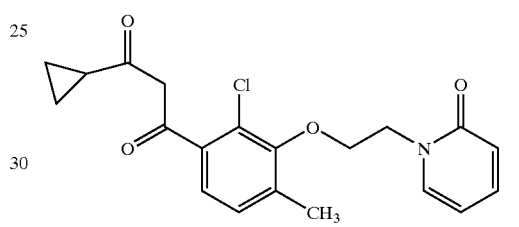

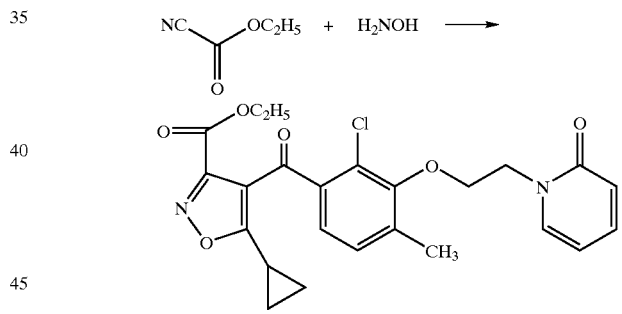

The formula (II) provides a general definition of the substituted benzoic acids to be used as starting materials in the process (a) according to the invention for preparing compounds of the general formula (I). In the general formula (II), n, A, R², R³ and R⁴ each preferably have those meanings which have already been mentioned above, in connection with the description of the compounds of the general formula (I) according to the invention, as being preferred, particularly preferred or very particularly preferred for n, A, R², R³ and R⁴.

The starting materials of the general formula (II) have hitherto not been disclosed in the literature; as novel substances, they also form part of the subject-matter of the present application.

The novel substituted benzoic acids—or else their derivatives, such as their esters, in particular the methyl esters and ethyl esters—are obtained when (α) Compounds of the Formula (IV)

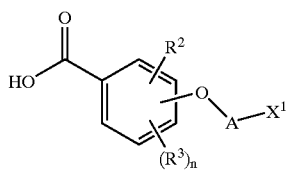

in which
n, A, $R^2$ and $R^3$ are each as defined above and
$X^1$ represents halogen (in particular fluorine, chlorine or bromine) or represents alkylsulphonyloxy (in particular methylsulphonyloxy or ethylsulphonyloxy),
or else their derivatives, such as their esters, in particular the methyl esters and ethyl esters
are reacted with heterocyclic compounds of the general formula (V)

$$H—R^4 \qquad (V)$$

in which
$R^4$ is as defined above,
if appropriate in the presence of an acid acceptor, such as, for example, potassium carbonate, and if appropriate in the presence of a diluent, such as, for example, acetone, butanone, acetonitrile, N,N-dimethyl-formamide or dimethyl sulphoxide, at temperatures between 10° C. and 150° C., followed, if appropriate, by further customary conversion reactions within the scope of the definition of the substituents (cf. the Preparation Examples),
or when (β) Compounds of the Formula (VI)

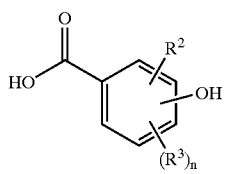

in which
n, $R^2$ and $R^3$ are each as defined above
or else their derivatives, such as their esters, in particular the methyl esters and ethyl esters
are reacted with hydroxyalkylheterocycles of the general formula (VII)

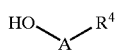 (VII)

in which
A and $R^4$ are each as defined above,
in the presence of condensing auxiliaries, such as, for example, diethyl azodicarboxylate and triphenylphosphine, if appropriate in the presence of a diluent, such as, for example, tetrahydrofuran at temperatures between −20° C. and +50° C., followed, if appropriate, by further customary conversion reactions within the scope of the definition of the substituents (cf. the Preparation Examples),
or when (γ) Compounds of the Formula (VI)

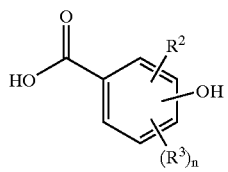

in which
n, $R^2$ and $R^3$ are each as defined above,
or else their derivatives, such as their esters, in particular the methyl esters and ethyl esters
are reacted with halogenoalkylheterocycles of the general formula (VIII)

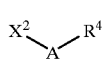 (VIII)

in which
A and $R^4$ are each as defined above and
$X^2$ represents halogen (in particular fluorine, chlorine or bromine), represents alkylsulphonyloxy (in particular methylsulphonyloxy or ethylsulphonyloxy), or represents arylsulphonyloxy (in particular p-tolylsulphonyloxy),
if appropriate in the presence of an acid acceptor, such as, for example, potassium carbonate or triethylamine, and if appropriate in the presence of a diluent, such as, for example, acetone, butanone, acetonitrile, N,N-dimethyl-formamide or dimethyl sulphoxide, at temperatures between 0° C. and 150° C., followed, if appropriate, by further customary conversion reactions within the scope of the definition of the substituents (cf. the Preparation Examples).

The formula (III) provides a general definition of the compounds further to be used as starting materials in the process (a) according to the invention for preparing compounds of the general formula (I). In the general formula (III), $R^1$ preferably has that meaning which has already been mentioned above, in connection with the description of the compounds of the general formula (I) according to the invention, as being preferred, particularly preferred or very particularly preferred for $R^1$.

The starting materials of the general formula (III) are known organic compounds.

The formula (Ia) provides a general definition of the substituted benzoyl ketones to be used as starting materials in the process (b) according to the invention for preparing compounds of the general formula (I). In the general formula (Ia), n, A, $R^2$, $R^3$, $R^4$ and $R^{11}$ each preferably have those meanings which have already been mentioned above, in connection with the description of the compounds of the general formula (I) according to the invention, as being preferred, particularly preferred or very particularly preferred for n, A, $R^2$, $R^3$, $R^4$ and $R^{11}$.

The starting materials of the general formula (Ia) are novel compounds according to the invention; they can be prepared by the process (a) according to the invention.

The process (a) according to the invention for preparing the novel substituted aryl ketones of the general formula (I) is, if appropriate, carried out using a dehydrating agent.

Suitable dehydrating agents are the customary chemicals suitable for binding water.

Examples of these which may be mentioned are dicyclohexylcarbodiimide and carbonyldiimidazole.

A particularly suitable dehydrating agent which may be mentioned is dicyclohexylcarbodiimide.

The process (a) according to the invention for preparing the novel substituted aryl ketones of the general formula (I) is, if appropriate, carried out using one or more reaction auxiliaries.

Examples of these which may be mentioned are sodium cyanide, potassium cyanide, acetone cyanohydrin, 2-cyano-2-(trimethylsilyloxy)-propane and trimethylsilyl cyanide.

The particularly suitable further reaction auxiliary which may be mentioned is trimethylsilyl cyanide.

The process (a) according to the invention for preparing the novel substituted aryl ketones of the general formula (I) is, if appropriate, carried out using a further reaction auxiliary. Suitable further reaction auxiliaries for the process according to the invention are, in general, basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]-octane (DABCO), 1,5-diazabicyclo[4.3.0]-non-5-ene (DBN), or 1,8-diazabicyclo[5.4.0]-undec-7-ene (DBU).

The process (b) according to the invention for preparing the compounds of the formula (I) is, if appropriate, carried out using orthoformic esters or N,N-dimethylformamide acetals. These compounds preferably contain alkyl groups having 1 to 4 carbon atoms, in particular methyl or ethyl. Examples which may be mentioned are trimethyl orthoformate, triethyl orthoformate, N,N-dimethyl-formamide dimethyl acetal and N,N-dimethyl-formamide diethylacetal.

The process (b) according to the invention for preparing compounds of the formula (I) is, if appropriate, carried out using cyanoformic esters. These compounds preferably contain alkyl groups having 1 to 4 carbon atoms, in particular methyl or ethyl. The examples which may be mentioned are methyl cyanoformate and ethyl cyanoformate.

The process (b) according to the invention for preparing compounds of the formula (I) is, if appropriate, carried out using (carbon disulphide and) alkylating agents. These compounds preferably contain alkyl groups having 1 to 4 carbon atoms, in particular methyl or ethyl. Examples which may be mentioned are methyl chloride, methyl bromide, methyl iodide, dimethyl sulphate, ethyl chloride, ethyl bromide, ethyl iodide and diethyl sulphate.

The process (b) according to the invention for preparing compounds of the formula (I) is carried using hydroxylamine or an acid adduct thereof. Hydroxylamine hydrochloride may be mentioned as preferred acid adduct.

The processes according to the invention for preparing the compounds of the general formula (I) are preferably carried out using diluents. Suitable diluents for carrying out the processes (a) and (b) according to the invention are especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethylether, diisopropylether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters, such as methyl acetate or ethyl acetate; sulphoxides, such as dimethylsulphoxide; alcohols, such as methanol, ethanol, n- or i-propanol, ethylene glycol monomethyl ether, ethylene glycol monoethyl ether, diethylene glycol monomethyl ether, diethylene glycol monoethyl ether.

When carrying out the processes (a) and (b) according to the invention, the reaction temperatures can be varied within a relatively wide range. In general, the processes are carried out at temperatures between 0° C. and 150° C., preferably between 10° C. and 120° C.

The processes (a) and (b) according to the invention are generally carried out under atmospheric pressure. However, it is also possible to carry out the processes according to the invention under elevated or reduced pressure—in general between 0.1 bar and 10 bar.

For carrying out the processes (a) and (b) according to the invention, the starting materials are generally employed in approximately equimolar amounts. However, it is also possible to use a relatively large excess of one of the components. The reaction is generally carried out in a suitable diluent and the reaction mixture is generally stirred at the required temperature for several hours. Work-up is carried out by customary methods (cf. the Preparation Examples).

The compounds of the formulae (IV), (V), (VI), (VII) and (VIII) to be used as starting materials in the process according to the invention for preparing compounds of the general formula (II) are known organic compounds.

The active compounds according to the invention can be used as defoliants, desiccants, haulm killers and, especially, as weed killers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

Dicotyledonous crops of the genera: Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.

Monocotyledonous weeds of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.

Monocotyledonous crops of the genera: *Allium*, Ananas, *Asparagus, Avena, Hordeum, Oryza, Panicum, Saccharum, Secale, Sorghum*, Triticale, *Triticum, Zea*.

However, the use of the active compounds according to the invention is in no way restricted to these genera, but also extends in the same manner to other plants.

The active compounds accordingly to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad active spectrum when used on the soil and on above-ground parts of plants. To a certain extent they are also suitable for the selective control of monocotyledonous and dicotyledonous weeds in monocotyledonous and dicotyledononscrops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or rage area according to customary treatment methods, for example by dipping, spraying, evaporating, atomizing, broadcasting, brushing-on and, in the case of propagation material, in particular in the case of seeds, furthermore by one- or multi-layer coating.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam-formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxyl methylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use colorants, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 percent by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example acetochlor, acifluorfen (-sodium), aclonifen, alachlor, alloxydim (-sodium), ametryne, amicarbazone, amidochlor, amidosulphuron, anilofos, asulam, atrazine, azafenidin, azimsulphuron, BAS-662H, beflubutamid, benazolin (-ethyl), benfuresate, bensulphuron (-methyl), bentazon, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulphuron, chlortoluron, cinidon (-ethyl), cinmethylin, cinosulphuron, clefoxydim, clethodim, clodinafop (-propargyl), clomazone, clomeprop, clopyralid, clopyrasulphuron (-methyl), cloransulam (-methyl), cumyluron, cyanazine, cybutryne, cycloate, cyclosulphamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachior, dimethametryn, dimethenamid, dimexyflam, dinitramine, diphenamid, diquat, dithiopyr, diuron, dymron, epropodan, EPTC, esprocarb, ethalfluralin, ethametsulphuron (-methyl), ethofumesate, ethoxyfen, ethoxysulphuron, etobenzanid, fenoxaprop (-P-ethyl), fentrazamide, flamprop (-isopropyl, -isopropyl-L, -methyl), flazasulphuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulphuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulphuron, glufosinate (-ammonium), glyphosate (-isopropylammonium), halosafen, haloxyfop (-ethoxyethyl, -P-methyl), hexazinone, imazamethabenz (-methyl), imazamethapyr, imazamox, imazapic, imazapyr, imazaquin, imazethapyr, imazosulphuron, iodosulphuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesosulphuron, mesotrione, metamitron, metazachlor, methabenzthiazuron, metobenzuron, metobromuron, (alpha-) metolachlor, metosulam, metoxuron, metribuzin, metsulphuron (-methyl), molinate, monolinuron, naproanilide, napropamide, neburon, nicosulphuron, norflurazon, orbencarb, oryzalin, oxadiargyl, oxadiazon, oxasulphuron, oxaziclomefone, oxyfluorfen, paraquat, pelargon acid, pendimethalin, pendralin, pentoxazone, phenmedipham, picolinafen, piperophos, pretilachlor, primisulphuron (-methyl), profluazol, prometryn, propachlor, propanil, propaquizafop, propisochlor, procarbazone (-sodium), propyzamide, prosulphocarb, prosulphuron, pyraflufen (-ethyl), pyrazogyl, pyrazolate, pyrazosulphuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop (-P-ethyl, -P-tefuryl), rimsulphuron, sethoxydim, simazine, simetryn, sulcotrione, sulphentrazone, sulphometuron (-methyl), sulphosate, sulphosulphuron, tebutam, tebuthiuron, tepraloxydim, terbuthylazine, terbutryn, thenylchlor, thiafluamide, thiazopyr, thidiazimin, thifensulphuron (-methyl), thiobencarb, tiocarbazil, tralkoxydim, triallate, triasulphuron, tribenuron (-methyl), triclopyr, tridiphane, trifluralin, trifloxysulphuron, triflusulphuron (-methyl), trito-sulphuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention is illustrated by the examples below.

PREPARATION EXAMPLES

Example 1

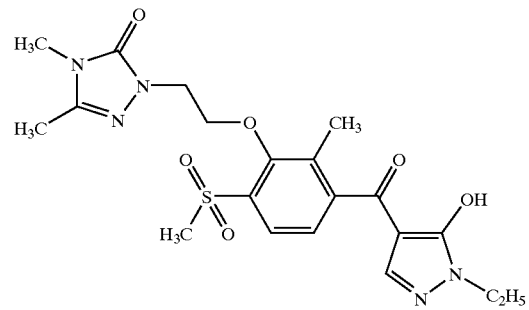

(Process (a))

0.30 g of (2.7 mmol) of 1-ethyl-5-hydroxy-pyrazole, 0.8 g (8.0 mmol) of triethylamine and a drop of N,N-dimethylformamide are added successively to a solution of 1.1 g (2.7 mmol) of 3-[2-(3',4'-dimethyl-1',2',4'-1H-triazolin-5'-on-1'-yl)-ethoxy]-2-methyl-4-methylsulphonyl-benzoyl chloride in 20 ml of dichloromethane. The mixture is stirred at room temperature (about 20° C.), for about 24 hours, the reaction solution is washed successively with 1N hydrochloric acid and saturated sodium chloride solution and dried over magnesium sulphate and the solvent is removed under water pump vacuum. The residue is dissolved in 30 ml of acetonitrile and, with slight cooling, admixed successively with 0.28 g (3.3 mmol) of 2-hydroxyl-2-methylpropionitrile and 1.4 g (14 mmol) of triethylamine. The mixture is stirred at room temperature for another 24 hours, the major part of the solvent is removed under water pump vacuum and the residue is dissolved in dichloromethane and 1N hydrochloric acid. The organic phase is separated off, washed with water and saturated sodium chloride solution, dried over magnesium sulphate and filtered. From the filtrate, the solvent is carefully distilled off under reduced pressure.

This gives 1.1 g (88% of theory) of 4-{3-[2-(3',4'-dimethyl-1',2',4'-1H-triazolin-5'-on-1'-yl)-ethyloxy]-2-methyl-4-methylsulphonyl-benzoyl}-1-ethyl-5-hydroxy-1H-pyrazole as an oily residue.

Log P: 1.23.

Example 2

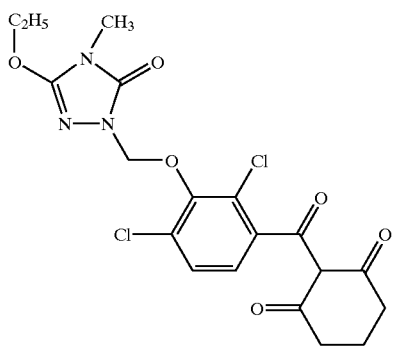

(Process (a))

1.95 g (5,4 mmol) of 3-(3'-ethoxy-4'-methyl-1',2',4'-1H-triazolin-5'-on-1'-yl)-methoxy-2,4-dichloro-benzoic acid are dissolved in 75 ml of acetonitrile and mixed with 0.61 g of 1,3-cyclohexanedione (5.4 mmol) and 1.33 g of dicyclohexylcarbodiimide (DCC, 1.2 equivalents). The mixture is stirred at room temperature (about 20° C.) for 15 hours, and 1.5 ml of triethylamine (2 equivalents) and 0.29 ml of trimethylsilyl cyanide (0.4 equivalents) are then added. After 2 hours at room temperature, the mixture is concentrated under water pump vacuum and the residue is stirred with 10% strength aqueous sodium carbonate solution and filtered off. The filtrate is shaken with diethylether and the aqueous phase is acidified with 2N hydrochloric acid. The precipitated product is extracted repeatedly with dichloromethane and the combined organic phases are dried over sodium sulphate, filtered and concentrated.

This gives 1.3 g (53% of theory) of 2-[3-(3'-ethoxy-4'-methyl-1',2',4'-1H-triazolin-5'-on-1'-yl)-methoxy-2,4-dichloro-benzoyl]-1,3-cyclohexanedione as a viscous resin. LogP=2.52.

Analogously to Examples 1 and 2, and in accordance with the general description of the preparation processes according to the invention, it is also possible to prepare, for example, the compounds of the general formula (I) listed in Table 1 below.

TABLE 1

Examples of the compounds of the formula (I)

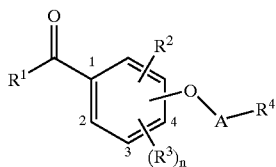

(I)

| Ex. No. | A | $R^1$ | (position) $R^2$ | (position) $(R^3)_n$ | (position) $OAR^4$) $R^4$ | Physical data |
|---|---|---|---|---|---|---|
| 3 | $CH_2$ | 2-methyl-3-hydroxy-cyclohex-2-enone | (2) Cl | (4) Cl | (3) 1-methyl-2-pyridinone | logP = 2.04[a] |
| 4 | $CH_2CH_2$ | 2-methyl-3-hydroxy-cyclohex-2-enone | (2) Cl | (4) Cl | (3) 3,4-dimethyl-1-methyl-triazolinone | logP = 1.92[a] |
| 5 | $CH_2CH_2$ | 1-ethyl-5-hydroxy-4-methyl-pyrazole | (2) Cl | (4) Cl | (3) 3,4-dimethyl-1-methyl-triazolinone | logP = 1.52[a] |
| 6 | $CH_2CH_2$ | 2-methyl-3-hydroxy-cyclohex-2-enone | (2) $CH_3$ | (4) Cl | (3) 3,4-dimethyl-1-methyl-triazolinone | logP = 1.93[a] |

TABLE 1-continued

Examples of the compounds of the formula (I)

(I)

| Ex. No. | A | R¹ | (position) R² | (position) (R³)n | (position OAR⁴) R⁴ | Physical data |
|---|---|---|---|---|---|---|
| 7 | $CH_2CH_2$ | 1-ethyl-5-hydroxy-4-methyl-pyrazol-3-yl | (2) $CH_3$ | (4) Cl | (3) 2,4-dimethyl-5-oxo-2,5-dihydro-1,2,4-triazol-3-yl | logP = 1.68[a] |
| 8 | $CH_2CH_2$ | 3-hydroxy-2-methyl-cyclohex-2-enon-1-yl | (2) Cl | (4) $SCH_3$ | (3) 2,4-dimethyl-5-oxo-2,5-dihydro-1,2,4-triazol-3-yl | logP = 1.94[a] |
| 9 | $CH_2CH_2$ | 1-ethyl-5-hydroxy-4-methyl-pyrazol-3-yl | (2) Cl | (4) $SCH_3$ | (3) 2,4-dimethyl-5-oxo-2,5-dihydro-1,2,4-triazol-3-yl | logP = 1.58[a] |
| 10 | $CH_2CH_2$ | 3-hydroxy-2-methyl-cyclohex-2-enon-1-yl | (2) $CH_3$ | (4) $SCH_3$ | (3) 2,4-dimethyl-5-oxo-2,5-dihydro-1,2,4-triazol-3-yl | logP = 1.91[a] |
| 11 | $CH_2CH_2$ | 3-hydroxy-2-methyl-cyclohex-2-enon-1-yl | (2) Cl | (4) $SO_2CH_3$ | (3) 2,4-dimethyl-5-oxo-2,5-dihydro-1,2,4-triazol-3-yl | logP = 1.65[a] |

TABLE 1-continued

Examples of the compounds of the formula (I)

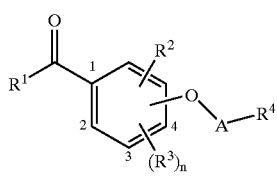

(I)

| Ex. No. | A | R¹ | (position) R² | (position) (R³)n | (position OAR⁴) R⁴ | Physical data |
|---|---|---|---|---|---|---|
| 12 | CH₂CH₂ | 1-ethyl-4-methyl-5-(4-bromobenzyloxy)pyrazole | (2) CH₃ | (4) Cl | (3) 2,4-dimethyl-5-oxo-2,5-dihydro-1,2,4-triazol-3-yl | logP = 2.07[a] |
| 13 | CH₂ | 2-methyl-3-hydroxycyclohex-2-enone | (2) Cl | (4) Cl | (3) 5-methylthio-2,4-dimethyl-2,5-dihydro-1,2,4-triazol-3(4H)-one-yl | logP = 2.44[a] |
| 14 | CH₂CH₂ | 1-ethyl-4-methyl-5-(4-bromobenzyloxy)pyrazole | (2) Cl | (4) SCH₃ | (3) 2,4-dimethyl-5-oxo-2,5-dihydro-1,2,4-triazol-3-yl | logP = 2.05[a] |
| 15 | CH₂CH₂ | 1-ethyl-4-methyl-5-hydroxypyrazole | (2) Cl | (4) Cl | (3) 5-methoxy-2,4-dimethyl-2,5-dihydro-1,2,4-triazol-3(4H)-one-yl | logP = 1.69[a] |
| 16 | CH₂CH₂ | 1-ethyl-4-methyl-5-hydroxypyrazole | (2) Cl | (4) Cl | (3) 5-methylthio-2,4-dimethyl-2,5-dihydro-1,2,4-triazol-3(4H)-one-yl | logP = 1.92[a] |

TABLE 1-continued

Examples of the compounds of the formula (I)

$$(I)$$

| Ex. No. | A | R¹ | (position) R² | (position) (R³)n | (position OAR⁴) R⁴ | Physical data |
|---|---|---|---|---|---|---|
| 17 | CH₂CH₂ | 1-ethyl-5-hydroxy-4-methylpyrazol-3-yl | (2) Cl | (4) Cl | (3) 3-methoxy-4-ethyl-1-methyl-1,2,4-triazol-5(4H)-one-3-yl | logP = 1.93[a] |
| 18 | CH₂CH₂ | 1-ethyl-5-hydroxy-4-methylpyrazol-3-yl | (2) Cl | (4) Cl | (3) 3-methoxymethyl-1,4-dimethyl-1,2,4-triazol-5(4H)-one | logP = 1.62[a] |
| 19 | CH₂CH₂ | 3-hydroxy-2-methylcyclohex-2-en-1-on-6-yl | (2) Cl | (4) Cl | (3) 3-methoxymethyl-1,4-dimethyl-1,2,4-triazol-5(4H)-one | logP = 2.06[a] |
| 20 | CH₂ | 1-ethyl-5-hydroxy-4-methylpyrazol-3-yl | (2) Cl | (4) SCH₃ | (3) 5-methylpyrrolidin-2-one-yl | (S enantiomer) logP = 1.60[a] |
| 21 | CH₂CH₂ | 3-hydroxy-2-methylcyclohex-2-en-1-on-6-yl | (2) Cl | (4) Cl | (3) 3-methylthio-1,4-dimethyl-1,2,4-triazol-5(4H)-one | logP = 2.39[a] |
| 22 | CH₂CH₂ | 3-hydroxy-2-methylcyclohex-2-en-1-on-6-yl | (2) Cl | (4) Cl | (3) 3-methoxy-4-ethyl-1-methyl-1,2,4-triazol-5(4H)-one | logP = 2.16[a] |

TABLE 1-continued
Examples of the compounds of the formula (I)
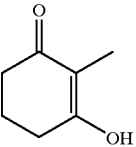
(I)
| Ex. No. | A | R¹ | (position) R² | (position) (R³)n | (position OAR⁴) R⁴ | Physical data |
|---|---|---|---|---|---|---|
| 23 | CH₂CH₂ | 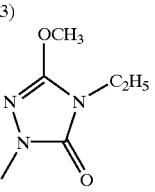 | (2) Cl | (4) Cl | (3) 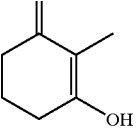 | logP = 2.40[a] |
| 24 | CH₂ | 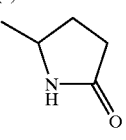 | (2) Cl | (4) SCH₃ | (3) 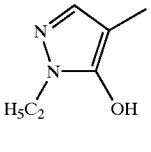 | (S enantiomer) logP = 1.98[a] |
| 25 | CH₂CH₂ | 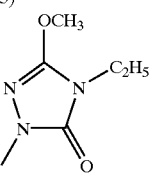 | (2) CH₃ | (4) Cl | (3) 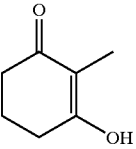 | logP = 1.88[a] |
| 26 | CH₂CH₂ | 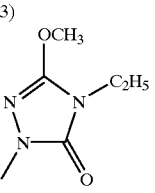 | (2) CH₃ | (4) Cl | (3) 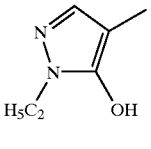 | logP = 2.15[a] |
| 27 | CH₂CH₂ | 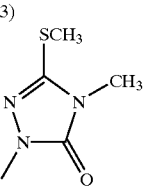 | (2) CH₃ | (4) Cl | (3) 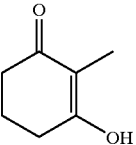 | logP = 2.11[a] |
| 28 | CH₂CH₂ | 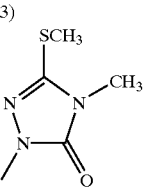 | (2) CH₃ | (4) Cl | (3) | logP = 2.38[a] |

TABLE 1-continued
Examples of the compounds of the formula (I)
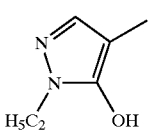
| Ex. No. | A | R¹ | (position) R² | (position) (R³)n | (position OAR⁴) R⁴ | Physical data |
|---|---|---|---|---|---|---|
| 29 | CH₂CH₂ | 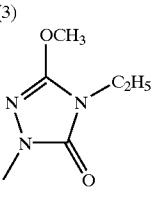 | (2) CH₃ | (4) Cl | (3) 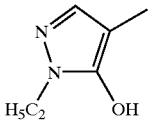 | logP = 2.12[a] |
| 30 | CH₂CH₂ | 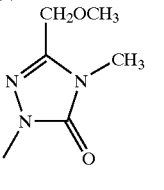 | (2) CH₃ | (4) Cl | (3) 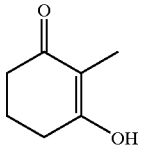 | logP = 1.78[a] |
| 31 | CH₂CH₂ | 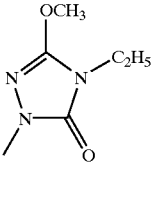 | (2) CH₃ | (4) Cl | (3) 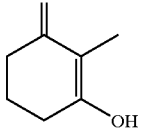 | logP = 2.38[a] |
| 32 | CH₂CH₂ | 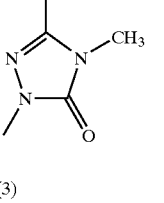 | (2) CH₃ | (4) Cl | (3) 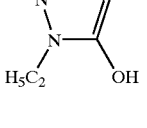 | logP = 2.04[a] |
| 33 | CH₂CH₂ | 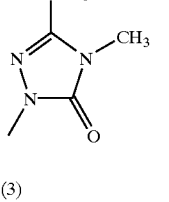 | (2) Cl | (4) SCH₃ | (3) 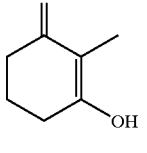 | logP = 1.97[a] |
| 34 | CH₂CH₂ | 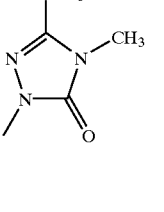 | (2) Cl | (4) SCH₃ | (3) | logP = 2.36[a] |

TABLE 1-continued

Examples of the compounds of the formula (I)

(I)

| Ex. No. | A | R¹ | (position) R² | (position) (R³)n | (position OAR⁴) R⁴ | Physical data |
|---|---|---|---|---|---|---|
| 35 | $CH_2$ | 1-ethyl-5-hydroxy-4-methylpyrazol-3-yl | (2) $CH_3$ | (4) Cl | (3) 5-methyl-2-oxopyrrolidin-5-yl | (S enantiomer) $[\alpha]_D^{20} = +2.3$ $\log P = 1.67^{a)}$ |
| 36 | $CH_2$ | 2-methyl-3-hydroxy-cyclohex-2-en-1-on-yl | (2) $CH_3$ | (4) Cl | (3) 5-methyl-2-oxopyrrolidin-5-yl | (S enantiomer) $\log P = 1.94^{a)}$ |
| 37 | $CH_2$ | 1-ethyl-5-hydroxy-4-methylpyrazol-3-yl | (2) $CH_3$ | (4) Cl | (3) 1,5-dimethyl-2-oxopyrrolidin-5-yl | (S enantiomer) $\log P = 1.85^{a)}$ |
| 38 | $CH_2$ | 2-methyl-3-hydroxy-cyclohex-2-en-1-on-yl | (2) $CH_3$ | (4) Cl | (3) 1,5-dimethyl-2-oxopyrrolidin-5-yl | (S enantiomer) $\log P = 2.10^{a)}$ |
| 39 | $CH_2$ | 2-methyl-3-hydroxy-cyclohex-2-en-1-on-yl | (2) Cl | (4) Cl | (3) 1,5-dimethyl-2-oxopyrrolidin-5-yl | (S enantiomer) $\log P = 2.12^{a)}$ |
| 40 | $CH_2$ | 1-ethyl-5-hydroxy-4-methylpyrazol-3-yl | (2) Cl | (4) Cl | (3) 1,5-dimethyl-2-oxopyrrolidin-5-yl | (S enantiomer) $\log P = 1.67^{a)}$ |
| 41 | $CH_2$ | 2-methyl-3-hydroxy-cyclohex-2-en-1-on-yl | (4) Cl | — | (2) 3-methylthio-4-methyl-1-methyl-5-oxo-1,2,4-triazol-3-yl | $\log P = 2.42^{a)}$ |

TABLE 1-continued

Examples of the compounds of the formula (I)

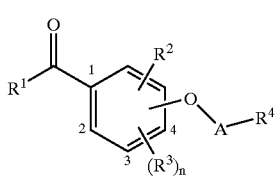

(I)

| Ex. No. | A | R¹ | (position) R² | (position) (R³)n | (position OAR⁴) R⁴ | Physical data |
|---|---|---|---|---|---|---|
| 42 | CH₂ | [pyrazole: N-N with H₅C₂, OH, CH₃] | (4) Cl | — | (2) [triazolinone with CH₃, N-CH₃, N-CH₃, =O] | logP = 1.65ᵃ⁾ |
| 43 | CH₂CH₂ | [pyrazole: N-N with H₅C₂, OH, CH₃] | (2) Cl | (4) SCH₃ | (3) [triazolinone with CH₂OCH₃, N-CH₃, N-CH₃, =O] | |
| 44 | CH₂CH₂ | [cyclohexanedione with CH₃, OH] | (2) Cl | (4) SCH₃ | (3) [triazolinone with CH₂OCH₃, N-CH₃, N-CH₃, =O] | logP = 2.05ᵃ⁾ |
| 45 | CH₂ | [pyrazole: N-N with H₅C₂, OH, CH₃] | (2) Cl | (4) SCH₃ | (3) [pyrrolidinone with N-CH₃] | (S enantiomer) logP = 1.68ᵃ⁾ |
| 46 | CH₂ | [cyclohexanedione with CH₃, OH] | (2) Cl | (4) SCH₃ | (3) [pyrrolidinone with N-CH₃] | (S enantiomer) logP = 2.13ᵃ⁾ |
| 47 | CH₂ | [cyclohexanedione with CH₃, OH] | (2) Cl | (4) Cl | (3) [pyrrolidinone N-H] | (S enantiomer) logP = 1.95ᵃ⁾ |
| 48 | CH₂ | [pyrazole: N-N with H₅C₂, OH, CH₃] | (2) Cl | (4) Cl | (3) [pyrrolidinone N-H] | (S enantiomer) logP = 1.51ᵃ⁾ |

TABLE 1-continued
Examples of the compounds of the formula (I)
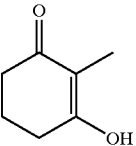
| Ex. No. | A | R¹ | (position) R² | (position) (R³)n | (position OAR⁴) R⁴ | Physical data |
|---|---|---|---|---|---|---|
| 49 | CH₂ | 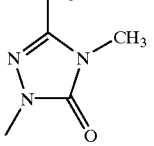 | (4) Cl | — | (2) 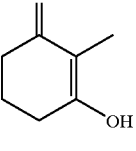 | logP = 1.92[a] |
| 50 | CH₂CH₂ | 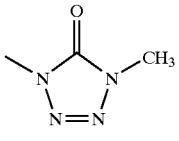 | (2) Br | (4) Br | (3) 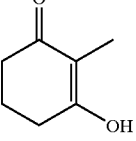 | $n_D^{20}$ = 1.5970 |
| 51 | CH₂CH₂ | 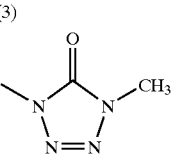 | (2) Cl | (4) Cl | (3) 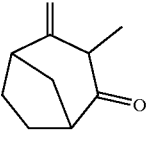 | $n_D^{20}$ = 1.5825 |
| 52 | CH₂CH₂ | 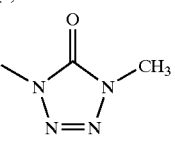 | (2) Cl | (4) Cl | (3) 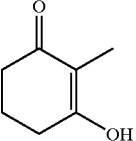 | $n_D^{20}$ = 1.5790 |
| 53 | CH₂CH₂ | 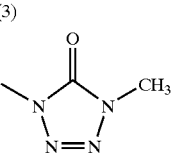 | (2) Cl | (4) SO₂CH₃ | (3) 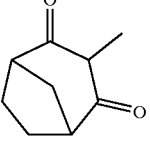 | m.p.: 69° C. |
| 54 | CH₂CH₂ | 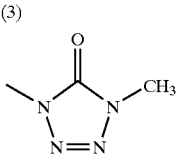 | (2) Cl | (4) SO₂CH₃ | (3) 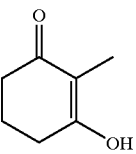 | m.p.: 62° C. |
| 55 | CH₂ | 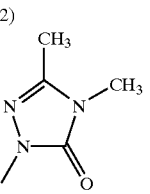 | (4) CF₃ | — | (2) | |

TABLE 1-continued

Examples of the compounds of the formula (I)

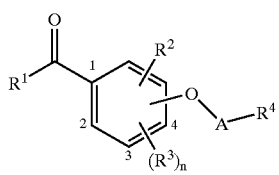

(I)

| Ex. No. | A | R¹ | (position) R² | (position) (R³)n | (position OAR⁴) R⁴ | Physical data |
|---|---|---|---|---|---|---|
| 56 | $CH_2$ | (1-ethyl-5-hydroxy-4-methyl-pyrazol-3-yl) | (4) $CF_3$ | — | (2) (3,5-dimethyl-4H-1,2,4-triazol-3(2H)-one-5-yl)methyl | |
| 57 | $CH_2$ | (2-methyl-3-hydroxy-cyclohex-2-enon-1-yl) | (4) $CF_3$ | — | (2) (4-methyl-3-methylthio-1-methyl-4H-1,2,4-triazol-3(2H)-one-5-yl)methyl | |
| 58 | $CH_2$ | (1-ethyl-5-hydroxy-4-methyl-pyrazol-3-yl) | (4) $CF_3$ | — | (2) (4-methyl-3-methylthio-1-methyl-4H-1,2,4-triazol-3(2H)-one-5-yl)methyl | |
| 59 | $CH_2$ | (2-methyl-3-hydroxy-cyclohex-2-enon-1-yl) | (2) Br | (4) Br | (3) (1,5-dimethyl-pyrrolidin-2-on-5-yl)methyl | (S enantiomer) |
| 60 | $CH_2$ | (1-ethyl-5-hydroxy-4-methyl-pyrazol-3-yl) | (2) Br | (4) Br | (3) (5-methyl-pyrrolidin-2-on-5-yl)methyl | (S enantiomer) logP = 1.56[a] |
| 61 | $CH_2$ | (2-methyl-3-hydroxy-cyclohex-2-enon-1-yl) | (2) Br | (4) Br | (3) (5-methyl-pyrrolidin-2-on-5-yl)methyl | (S enantiomer) logP = 2.02[a] |

The log P values given in Table 1 were determined in accordance with EEC Directive 79/831 V.A8 by HPLC (High Performance Liquid Chromatography) on a reversed-phase column (C 18). Temperature: 43° C.

(a) Mobile phases for the determination in the acidic range: 0.1% aqueous phosphoric acid, acetonitrile; linear gradient of 10% acetonitrile to 90% acetonitrile—the corresponding data in Table 1 are labelled [a].

(b) Mobile phases for the determination in the neutral range: 0.01 molar aqueous phosphate buffer solution, acetonitrile, linear gradient from 10% acetonitrile to 90% acetonitrile—the corresponding data in Table 1 are labelled [b].

Calibration was carried out using unbranched alkan-2-ones (with 3 to 16 carbon atoms) whose log P values are known (determination of the log P values by the retention times using linear interpolation between two successive alkanones).

The lambda-max values were determined in the maxima of the chromatographic signals using UV spectra from 200 nm to 400 nm.

Starting Materials of the Formula (II)

Example (II-1)

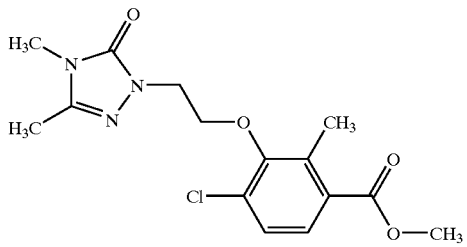

Step 1

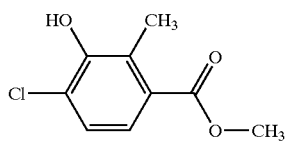

Over a period of 4 to 6 hours, 43 g (0.606 mol) of chlorine gas are introduced into a boiling solution of 100 g (0.6 mol) of methyl 3-hydroxy-2-methyl-benzoate and 0.4 ml of diisopropylamine in 800 ml of 1,2-dichloro-ethane. After cooling, the solution is washed successively with in each case 200 ml of 5% strength sodium hydrogen sulphite solution and with saturated sodium chloride solution, the organic phase is dried over magnesium sulphate and the solvent is removed under water pump vacuum. The dark-brown oil obtained as the residue is admixed with 30 ml of diethyl ether and cooled to from 0° to 4° C. for crystallization. The precipitated crystals are isolated by filtration with suction, washed with a little cold diethyl ether and dried under reduced pressure at 30° C.

This gives 46.6 g (39% of theory) of methyl 4-chloro-3-hydroxy-2-methyl-benzoate.

Log P: 2.14.

Using, instead of methyl 3-hydroxy-2-methyl-benzoate, the corresponding ethyl ester, ethyl 4-chloro-3-hydroxy-2-methyl-benzoate is obtained by the same process.

Melting point: 51° C.

Step 2

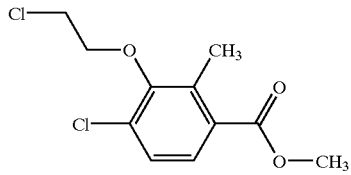

A solution of 25 g (0.125 mol) of methyl 4-chloro-3-hydroxy-2-methyl-benzoate in 400 ml of acetonitrile is admixed successively with 34.2 g (0.248 mol) of powdered anhydrous potassium carbonate and 29.3 g (0.125 mol) of 2-chloro-ethanol-p-toluene sulphonate. The reaction mixture is heated at 70° C. for about 7 hours and then allowed to cool, and the major part of the solvent is removed under water pump vacuum. The residue is dissolved in 200 ml of dichloromethane and 300 ml of water. The organic phase is separated off, washed with water, dried over magnesium sulphate and filtered. From the filtrate, the solvent is carefully distilled off under reduced pressure.

This gives 32.5 g (99% of theory) of methyl 4-chloro-3-(2-chloro-ethoxy)-2-methyl-benzoate as a dark oil.

Log P=3.52.

Step 3

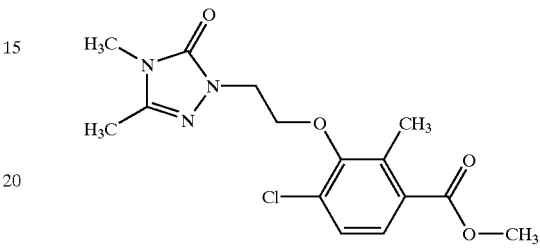

A solution of 16.0 g (60.8 mmol) of methyl 4-chloro-3-(2-chloro-ethoxy)-2-methyl-benzoate in 70 ml of dimethyl sulphoxide is admixed successively with 18.4 g (0.133 mol) of powdered anhydrous potassium carbonate and 6.9 g (60.8 mmol) of 3,4-dimethyl-1,2,4-triazolin-5-one. The reaction mixture is heated at 90° C., for about 6 hours and then allowed to cool, and the major part of the solvent is removed under water pump vacuum. The residue is dissolved in 140 ml of dichloromethane and 60 ml of water. The organic phase is separated off, washed with water, dried over magnesium sulphate and concentrated under water pump vacuum. The oily residue is stirred with 25 ml of petroleum ether. The resulting crystalline product is isolated by filtration with suction.

This gives 18.5 g (80% of theory) of methyl 4-chloro-3-[2-(3',4'-dimethyl-1',2',4'-1H-triazolin-5'-on-1'-yl)-ethoxy]-2-methyl-benzoate.

Log P: 1.94.

Example (II-2)

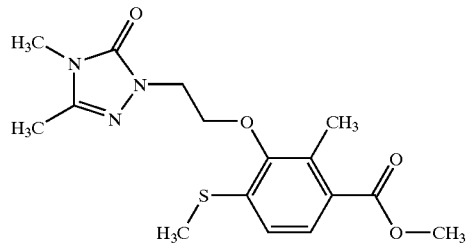

With ice-cooling, 3.3 g (44.5 mmol) of sodium methyl mercaptide are added to a solution of 12.4 g (36.5 mmol) of methyl 4-chloro-3-[2-(3',4'-dimethyl-1',2',4'-1H-triazolin-5'-on-1'-yl)-ethoxyl]-2-methyl-benzoate in 100 ml of N,N-dimethyl-formamide. The mixture is stirred at room temperature (about 20° C.) for about 6 hours, and the major part of the solvent is removed under water pump vacuum. The residue is dissolved in 300 ml of ethyl acetate and 200 ml of water. The organic phase is separated off, washed with water, dried over magnesium sulphate and filtered. From the filtrate, the solvent is carefully distilled off under reduced pressure.

This gives 5.4 g (42% of theory) of methyl 3-[2-(3',4'-dimethyl-1',2',4'-1H-triazolin-5'-on-1'-yl)-ethoxy]-2-methyl-4-methylthio-benzoate.

Log P=1.89.

Example (II-3)

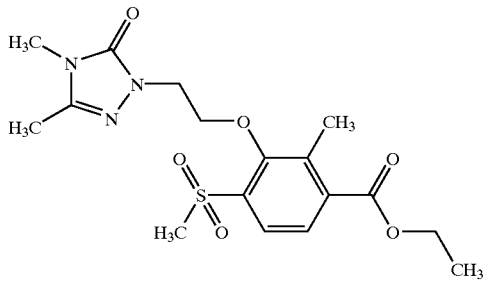

10 mg of ammonium molybdate tetrahydrate and 17.3 g (178 mmol) of a 35% strength aqueous hydrogen peroxide solution are added to a solution of 12.3 g (33.7 mmol) of ethyl 3-[2-(3',4'-dimethyl-1',2',4'-1H-triazolin-5'-on-1'-yl)-ethoxy]-2-methyl-4-methylthio-benzoate in 40 ml of acetic acid. The reaction mixture is heated at from 50° to 60° C. for about 6 hours, diluted with water and extracted with ethyl acetate. The organic phase is separated off, washed successively with water, sodium bicarbonate solution, sodium thiosulphate solution and again with water, dried over magnesium sulphate and filtered. From the filtrate, the solvent is carefully distilled off under reduced pressure.

This gives 12.3 g (92% of theory) of ethyl 3-[2-(3',4'-dimethyl-1',2',4'-1H-triazolin-5'-on-1'-yl)-ethoxy]-2-methyl-4-methylsulphonyl-benzoate.

Log P=1.76.

Example (II-4)

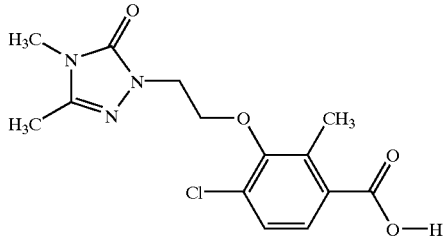

1.2 g (30 mmol) of a solution of sodium hydroxide in 20 ml of water are added to a solution of 6.5 g (19.0 mmol) of methyl 4-chloro-3-[2-(3',4'-dimethyl-1',2',4'-1H-triazolin-5'-on-1'-yl)-ethoxy]-2-methyl-benzoate in 40 ml of ethanol. The solution is stirred at room temperature (about 20° C.) for about 24 hours, and the major part of the solvent is removed under water pump vacuum. The residue is dissolved in water and acidified with hydrochloric acid. The resulting suspension is extracted with ethyl acetate and the organic phase is separated off, washed with saturated sodium chloride solution, dried over magnesium sulphate and filtered. From the filtrate the solvent is carefully distilled off under reduced pressure.

This gives 5.9 g (95% of theory) of 4-chloro-3-[2-(3',4'-dimethyl-1',2',4'-1H-triazolin-5'-on-1'-yl)-ethoxy]-2-methyl-benzoic acid.

Log P=1.37.

Example (II-5)

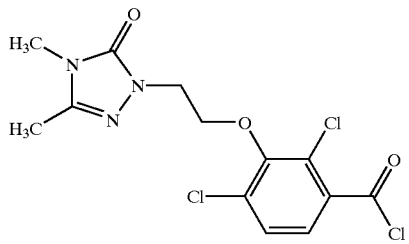

2.3 g (6.65 mmol) of 2,4-dichloro-3-[2-(3',4'-dimethyl-1',2',4'-1H-triazolin-5'-on-1'-yl)-ethoxy]-2-benzoic acid in 10 ml of thionyl chloride are heated at 70° C. for about 1.5 hours. The reaction solution is allowed to cool and the excess thionyl chloride is removed under reduced pressure.

This gives 2.4 g (100% of theory) of 2,4-dichloro-3-[2-(3',4'-dimethyl-1',2',4'-1H-triazolin-5'-on-1'-yl)-ethoxy]-2-benzoyl chloride.

Log P=1.24.

Example (II-6)

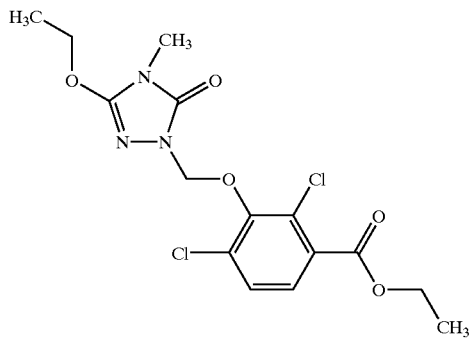

5 g (21.3 mmol) of ethyl 2,4-dichloro-3-hydroxy-benzoate are dissolved in 200 ml of tetrahydrofuran and admixed with 3.68 g (21.3 mmol) of 1-hydroxymethyl-3-ethoxy-4-methyl-1,2,4-triazolin-5-one. 5.58 g (21.3 mmol) of triphenylphosphine are added, and at 0° C., 4.4 g of 85% diethyl diazo-dicarboxylate are then added dropwise. The resulting solution is stirred overnight, concentrated under water pump vacuum and filtered through silica gel (ethyl acetate/hexane). The filtrate is concentrated and mixed with diethyl ether. The solid that separates off is filtered off, and the solvent is carefully distilled off from the filtrate under reduced pressure.

This gives 6.8 g (82% of theory) of ethyl 3-(3'-ethoxy-4'-methyl-1',2',4'-1H-triazolin-5'-on-1'-yl)-methoxy-2,4-dichloro-benzoate as a viscous oil.

Log P=2.77.

Example (II-7)

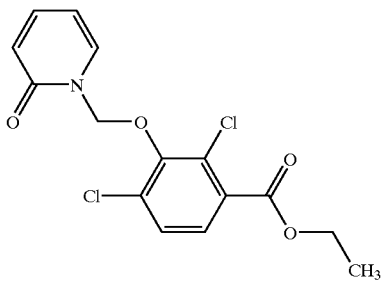

2 g (8.5 mmol) of ethyl 2,4-dichloro-3-hydroxy-benzoate are dissolved in 30 ml of acetonitrile and mixed successively with 0.86 g (8.5 mmol) of triethylamine and 1.2 g (8.5 mmol) of N-chloromethyl-2-pyridone. The resulting mixture is stirred at 60° C. for 7 hours, admixed with water and extracted with ethyl acetate. The organic phase is separated off, washed with saturated sodium chloride solution, dried over magnesium sulphate and filtered. The solvent is carefully distilled off under reduced pressure.

This gives 2.4 g (82% of theory) of ethyl 2,4-dichloro-3-(1H-pyrid-2-on-1-yl)-methoxy-benzoate.

Example (II-8)

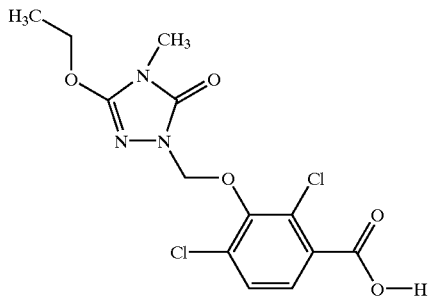

6.4 g (16.3 mmol) of ethyl 3-(3'-ethoxy-4'-methyl-1',2',4'-1H-triazolin-5'-on-1'-yl)-methoxy-2,4-dichloro-benzoate are stirred in a mixture of 250 ml of cyclohexane and 25 ml of ethylene glycol monomethyl ether in the presence of 0.91 g of powdered potassium hydroxide at room temperature (about 20° C.) for 15 hours. The mixture is diluted with water and acidified with 2N hydrochloric acid. The precipitated solid is isolated by filtration with suction.

This gives 4.05 g (69% of theory) of 3-(3'-ethoxy-4'-methyl-1',2',4'-1H-triazolin-5'-on-1'-yl)-methoxy-2,4-dichloro-benzoic acid.

log P: 1.74.

Analogously to Examples (II-1) to (II-8), it is also possible to prepare, for example, the compounds of the general formula (II) listed in Table 2 below, or reactive derivatives thereof—cf. formula (IIA),

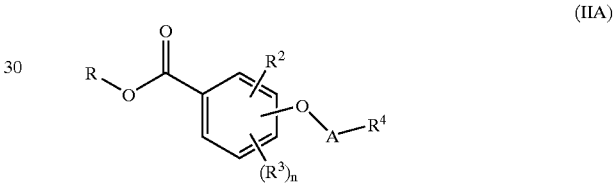

(IIA)

where

R has one of the meanings listed in the Table below.

TABLE 2

| | | Examples of compounds of the formula (II) or (IIA) | | | | |
|---|---|---|---|---|---|---|
| Ex. No. | A | (position) $R^2$ | (position) $(R^3)_n$ | (position $OAR^4$) $R^4$ | R | Physical data |
| II-9 | $CH_2CH_2$ | (2) $CH_3$ | (4) Cl | (3) ![triazolinone] | $C_2H_5$ | logP = 2.25[a] |
| II-10 | $CH_2CH_2$ | (2) $CH_3$ | (4) $SCH_3$ | (3) ![triazolinone] | $C_2H_5$ | logP = 2.16[a] |

TABLE 2-continued

Examples of compounds of the formula (II) or (IIA)

| Ex. No. | A | (position) R² | (position) (R³)ₙ | (position OAR⁴) R⁴ | R | Physical data |
|---|---|---|---|---|---|---|
| II-11 | CH₂CH₂ | (2) CH₃ | (4) SO₂CH₃ | (3) triazolinone with CH₃, CH₃, CH₃ | CH₃ | logP = 1.48[a] |
| II-12 | CH₂CH₂ | (2) CH₃ | (4) SCH₃ | (3) triazolinone with CH₃, CH₃, CH₃ | H | logP = 1.33[a] |
| II-13 | CH₂CH₂ | (2) CH₃ | (4) SO₂CH₃ | (3) triazolinone with CH₃, CH₃, CH₃ | H | logP = 0.92[a] |
| II-14 | CH₂CH₂ | (2) Cl | (4) Cl | (3) triazolinone with CH₃, CH₃, CH₃ | C₂H₅ | logP = 2.08[a] |
| II-15 | CH₂CH₂ | (2) Cl | (4) Cl | (3) triazolinone with CH₃, CH₃, CH₃ | H | logP = 1.23[a] |
| II-16 | CH₂CH₂ | (2) SCH₃ | (4) SCH₃ | (3) triazolinone with CH₃, CH₃, CH₃ | C₂H₅ | logP = 2.13[a] |
| II-17 | CH₂CH₂ | (2) Cl | (4) SCH₃ | (3) triazolinone with CH₃, CH₃, CH₃ | C₂H₅ | logP = 2.09[a] |

TABLE 2-continued

Examples of compounds of the formula (II) or (IIA)

| Ex. No. | A | (position) R² | (position) (R³)ₙ | (position OAR⁴) R⁴ | R | Physical data |
|---|---|---|---|---|---|---|
| II-18 | CH₂CH₂ | (2) Cl | (4) SCH₃ | (3) triazolinone with CH₃, CH₃ | H | logP = 1.27[a] |
| II-19 | CH₂CH₂ | (2) Cl | (4) SOCH₃ | (3) triazolinone with CH₃, CH₃ | H | logP = 0.59[a] |
| II-20 | CH₂CH₂ | (2) Cl | (4) SO₂CH₃ | (3) triazolinone with CH₃, CH₃ | C₂H₅ | logP = 1.72[a] |
| II-21 | CH₂CH₂ | (2) Cl | (4) SO₂CH₃ | (3) triazolinone with CH₃, CH₃ | H | logP = 0.77[a] |
| II-22 | CH₂CH₂ | (2) SO₂CH₃ | (4) SO₂CH₃ | (3) triazolinone with CH₃, CH₃ | H | logP = 0.46[a] |
| II-23 | CH₂CH₂ | (2) Cl | (4) SOCH₃ | (3) triazolinone with CH₃, CH₃ | C₂H₅ | logP = 1.49[a] |
| II-24 | CH₂CH₂ | (2) CH₃ | (4) SO₂CH₃ | (3) triazolinone with CH₃, CH₃ | H (xHCl) | logP = 0.95[a] |

TABLE 2-continued

Examples of compounds of the formula (II) or (IIA)

| Ex. No. | A | (position) R² | (position) (R³)ₙ | (position OAR⁴) R⁴ | R | Physical data |
|---|---|---|---|---|---|---|
| II-25 | CH₂CH₂ | (2) Cl | (4) SO₂CH₃ | (3) 3,4-dimethyl-5-oxo-4,5-dihydro-1H-1,2,4-triazol-1-yl (N1-methyl, C3-methyl, N4-methyl, C5=O) | H (xHCl) | logP = 0.83[a] |
| II-26 | CH₂CH₂ | (2) CH₃ | (4) SCH₃ | (3) 3,4-dimethyl-5-oxo-4,5-dihydro-1H-1,2,4-triazol-1-yl | H (xHCl) | logP = 1.34[a] |
| II-27 | CH₂CH₂ | (2) Cl | (4) SCH₃ | (3) 3,4-dimethyl-5-oxo-4,5-dihydro-1H-1,2,4-triazol-1-yl | H (xHCl) | logP = 1.27[a] |
| II-28 | CH₂CH₂ | (2) CH₃ | (4) Cl | (3) 3,4-dimethyl-5-oxo-4,5-dihydro-1H-1,2,4-triazol-1-yl | H (xHCl) | logP = 1.37[a] |
| II-29 | CH₂ | (2) Cl | (4) Cl | (3) 3-methylthio-4-methyl-5-oxo-4,5-dihydro-1H-1,2,4-triazol-1-yl | C₂H₅ | logP = 2.69[a] |
| II-30 | CH₂ | (2) CH₃ | (4) Cl | (3) 1-methyl-2,5-dioxopyrrolidin-1-yl | CH₃ | logP = 2.13[a] |
| II-31 | CH₂ | (2) Cl | (4) Cl | (3) 3-methylthio-4-methyl-5-oxo-4,5-dihydro-1H-1,2,4-triazol-1-yl | H | logP = 1.68[a] |
| II-32 | CH₂ | (2) Cl | (4) Cl | (3) 1-methyl-2-oxo-1,2-dihydropyridin-1-yl | H | ¹H-NMR (DMSO-D6). δ): 5.89 ppm (s, CH₂) |

TABLE 2-continued

Examples of compounds of the formula (II) or (IIA)

| Ex. No. | A | (position) R² | (position) (R³)ₙ | (position OAR⁴) R⁴ | R | Physical data |
|---|---|---|---|---|---|---|
| II-33 | CH₂CH₂ | (2) Cl | (4) Cl | (3) 3-OCH₃, 4-CH₃, 1-N-methyl triazolinone | C₂H₅ | logP = 2.40[a] |
| II-34 | CH₂CH₂ | (2) Cl | (4) Cl | (3) 3-OCH₃, 4-CH₃, 1-N-methyl triazolinone | H | logP = 1.52[a] |
| II-35 | CH₂CH₂ | (2) Cl | (4) Cl | (3) 3-SCH₃, 4-CH₃, 1-N-methyl triazolinone | C₂H₅ | logP = 2.66[a] |
| II-36 | CH₂CH₂ | (2) Cl | (4) Cl | (3) 3-SCH₃, 4-CH₃, 1-N-methyl triazolinone | H | logP = 1.72[a] |
| II-37 | CH₂CH₂ | (2) Cl | (4) Cl | (3) 3-OCH₃, 4-C₂H₅, 1-N-methyl triazolinone | C₂H₅ | logP = 2.68[a] |
| II-38 | CH₂CH₂ | (2) Cl | (4) Cl | (3) 3-OCH₃, 4-C₂H₅, 1-N-methyl triazolinone | H | logP = 1.73[a] |
| II-39 | CH₂CH₂ | (2) Cl | (4) Cl | (3) 3-CH₂OCH₃, 4-CH₃, 1-N-methyl triazolinone | C₂H₅ | logP = 2.28[a] |

TABLE 2-continued
Examples of compounds of the formula (II) or (IIA)
| Ex. No. | A | (position) R² | (position) (R³)ₙ | (position OAR⁴) R⁴ | R | Physical data |
|---|---|---|---|---|---|---|
| II-40 | CH₂CH₂ | (2) Cl | (4) Cl | (3) 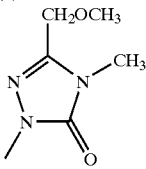 | H | logP = 1.45[a)] |
| II-41 | CH₂CH₂ | (2) CH₃ | (4) Cl | (3) 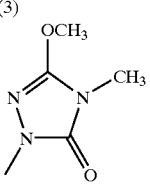 | CH₃ | logP = 2.17[a)] |
| II-42 | CH₂CH₂ | (2) CH₃ | (4) Cl | (3) 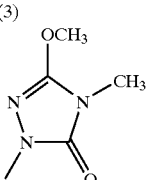 | H | logP = 1.78[a)] |
| II-43 | CH₂CH₂ | (2) CH₃ | (4) Cl | (3) 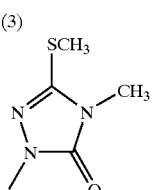 | CH₃ | logP = 2.44[a)] |
| II-44 | CH₂CH₂ | (2) CH₃ | (4) Cl | (3) 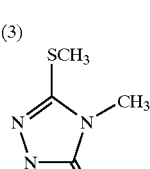 | H | logP = 1.75[a)] |
| II-45 | CH₂CH₂ | (2) CH₃ | (4) Cl | (3) 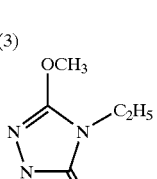 | CH₃ | logP = 2.46[a)] |
| II-46 | CH₂CH₂ | (2) CH₃ | (4) Cl | (3) 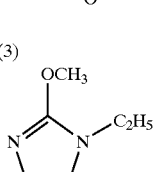 | H | logP = 1.79[a)] |

TABLE 2-continued

Examples of compounds of the formula (II) or (IIA)

| Ex. No. | A | (position) R² | (position) (R³)ₙ | (position OAR⁴) R⁴ | R | Physical data |
|---|---|---|---|---|---|---|
| II-47 | CH₂CH₂ | (2) CH₃ | (4) Cl | (3) [triazolinone with CH₂OCH₃, CH₃, CH₃] | CH₃ | logP = 2.06ᵃ⁾ |
| II-48 | CH₂CH₂ | (2) CH₃ | (4) Cl | (3) [triazolinone with CH₂OCH₃, CH₃, CH₃] | H | logP = 1.49ᵃ⁾ |
| II-49 | CH₂CH₂ | (2) Cl | (4) SCH₃ | (3) [triazolinone with SCH₃, CH₃, CH₃] | C₂H₅ | logP = 2.59ᵃ⁾ |
| II-50 | CH₂CH₂ | (2) Cl | (4) SCH₃ | (3) [triazolinone with SCH₃, CH₃, CH₃] | H | logP = 1.64ᵃ⁾ |
| II-51 | CH₂CH₂ | (2) Cl | (4) SCH₃ | (3) [triazolinone with CH₂OCH₃, CH₃, CH₃] | C₂H₅ | logP = 2.22ᵃ⁾ |
| II-52 | CH₂CH₂ | (2) Cl | (4) SCH₃ | (3) [triazolinone with CH₂OCH₃, CH₃, CH₃] | H | logP = 1.37ᵃ⁾ |
| II-53 | CH₂ | (2) Cl | (4) SCH₃ | (3) [pyrrolidinone] | C₂H₅ | (S enantiomer) logP = 2.17ᵃ⁾ |

TABLE 2-continued

Examples of compounds of the formula (II) or (IIA)

| Ex. No. | A | (position) R² | (position) (R³)ₙ | (position OAR⁴) R⁴ | R | Physical data |
|---|---|---|---|---|---|---|
| II-54 | $CH_2$ | (2) Cl | (4) $SCH_3$ | (3) 5-methyl-pyrrolidin-2-one (NH) | H | (S enantiomer) logP = 1.31[a)] |
| II-55 | $CH_2$ | (2) Cl | (4) $SCH_3$ | (3) 1,5-dimethyl-pyrrolidin-2-one | $C_2H_5$ | (S enantiomer) logP = 2.35[a)] |
| II-56 | $CH_2$ | (2) Cl | (4) $SCH_3$ | (3) 1,5-dimethyl-pyrrolidin-2-one | H | (S enantiomer) logP = 1.44[a)] |
| II-57 | $CH_2$ | (2) $CH_3$ | (4) Cl | (3) 5-methyl-pyrrolidin-2-one (NH) | $C_2H_5$ | (S enantiomer) logP = 1.95[a)] |
| II-58 | $CH_2$ | (2) $CH_3$ | (4) Cl | (3) 5-methyl-pyrrolidin-2-one (NH) | H | (S enantiomer) logP = 1.39[a)] |
| II-59 | $CH_2$ | (2) $CH_3$ | (4) Cl | (3) 1,5-dimethyl-pyrrolidin-2-one | $C_2H_5$ | (S enantiomer) logP = 2.18[a)] |
| II-60 | $CH_2$ | (2) $CH_3$ | (4) Cl | (3) 1,5-dimethyl-pyrrolidin-2-one | H | (S enantiomer) logP = 1.55[a)] |
| II-61 | $CH_2$ | (2) Cl | (4) Cl | (3) 5-methyl-pyrrolidin-2-one (NH) | $C_2H_5$ | (S enantiomer) logP = 2.15[a)] |
| II-62 | $CH_2$ | (2) Cl | (4) Cl | (3) 5-methyl-pyrrolidin-2-one (NH) | H | (S enantiomer) logP = 1.28[a)] |

TABLE 2-continued

Examples of compounds of the formula (II) or (IIA)

| Ex. No. | A | (position) R² | (position) (R³)ₙ | (position OAR⁴) R⁴ | R | Physical data |
|---|---|---|---|---|---|---|
| II-63 | CH₂ | (2) Cl | (4) Cl | (3) 1-methyl-5-methylpyrrolidin-2-one | C₂H₅ | (S enantiomer) |
| II-64 | CH₂ | (2) Cl | (4) Cl | (3) 1-methyl-5-methylpyrrolidin-2-one | CH₃ | (S enantiomer) $n_D^{20} = -20.4$ logP = 2.01[a)] |
| II-65 | CH₂ | (2) Cl | (4) Cl | (3) 1-methyl-5-methylpyrrolidin-2-one | H | (S enantiomer) logP = 1.42[a)] |
| II-66 | CH₂ | (4) Cl | — | (2) 5-SCH₃-4-methyl-2-methyl-1,2,4-triazol-3(4H)-one | CH₃ | logP = 2.33[a)] |
| II-67 | CH₂ | (4) Cl | — | (2) 5-SCH₃-4-methyl-2-methyl-1,2,4-triazol-3(4H)-one | H | logP = 1.81[a)] |
| II-68 | CH₂ | (4) Cl | — | (2) 5-CH₃-4-methyl-2-methyl-1,2,4-triazol-3(4H)-one | CH₃ | logP = 2.23[a)] |
| II-69 | CH₂ | (4) Cl | — | (2) 5-OCH₃-4-methyl-2-methyl-1,2,4-triazol-3(4H)-one | CH₃ | logP = 2.07[a)] |
| II-70 | CH₂ | (4) Cl | — | (2) 5-CH₃-4-methyl-2-methyl-1,2,4-triazol-3(4H)-one | H | logP = 1.36[a)] |

TABLE 2-continued

Examples of compounds of the formula (II) or (IIA)

| Ex. No. | A | (position) R² | (position) (R³)ₙ | (position OAR⁴) R⁴ | R | Physical data |
|---|---|---|---|---|---|---|
| II-71 | CH₂ | (4) CF₃ | — | (2) 3,4-dimethyl-5-oxo-4,5-dihydro-1H-1,2,4-triazol-1-yl | CH₃ | |
| II-72 | CH₂ | (4) CF₃ | — | (2) 3,4-dimethyl-5-oxo-4,5-dihydro-1H-1,2,4-triazol-1-yl | H | |
| II-73 | CH₂ | (4) CF₃ | — | (2) 4-methyl-3-methylthio-5-oxo-4,5-dihydro-1H-1,2,4-triazol-1-yl | CH₃ | |
| II-74 | CH₂ | (4) CF₃ | — | (2) 4-methyl-3-methylthio-5-oxo-4,5-dihydro-1H-1,2,4-triazol-1-yl | H | |
| II-75 | CH₂ | (2) Br | (4) Br | (3) 5-methyl-2-oxopyrrolidin-1-yl | C₂H₅ | (S enantiomer) logP = 2.20ª⁾ |
| II-76 | CH₂ | (2) Br | (4) Br | (3) 1,5-dimethyl-2-oxopyrrolidin-1-yl | C₂H₅ | (S enantiomer) logP = 2.46ª⁾ |
| II-77 | CH₂ | (2) Br | (4) Br | (3) 5-methyl-2-oxopyrrolidin-1-yl | H | (S enantiomer) logP = 1.34ª⁾ |
| II-78 | CH₂ | (2) Br | (4) Br | (3) 1,5-dimethyl-2-oxopyrrolidin-1-yl | H | (S enantiomer) logP = 1.49ª⁾ |

The compound listed in Table 2 as Example (II-35) can be prepared, for example, as follows:

Example (II-35)

Step 1

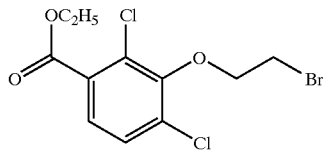

A solution of 15 g (68 mmol) of ethyl 2,4-dichloro-3-hydroxy-benzoate in 80 ml of N,N-dimethyl-formamide is admixed successively with 19 g (137 mmol) of potassium carbonate (powder), 38.6 g (205 mmol) of 1,2-dibromo-ethane and 0.4 g of sodium iodide. The mixture is heated at 80° C. for 2 hours and then allowed to cool to room temperature and shaken with 350 ml of diethyl ether. The organic phase is washed with water, 10% strength aqueous sodium hydroxide solution and finally with 10% strength hydrochloric acid and then dried with sodium sulphate and filtered. From the filtrate, the solvent is carefully distilled off under reduced pressure.

This gives 22.2 g (95% of theory) of ethyl 2,4-dichloro-3-(2-bromo-ethoxy)-benzoate as an oily residue (logP= $3.98^{a)}$).

Step 2

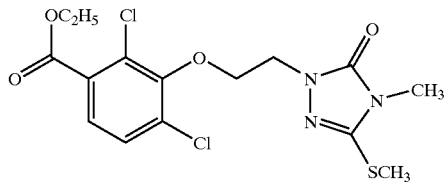

A solution of 18 g (93 mmol) of ethyl 2,4-dichloro-3-(2-bromo-ethoxy)-benzoate in 100 ml of N,N-dimethyl-formamide is admixed successively with 14.6 g (106 mmol) of potassium carbonate (powder), 19.3 g (133 mmol) of 3-methylthio-4-methyl-1,2,4-triazolin-5-one and 0.5 g of sodium iodide. The mixture is heated at 80° C. for 4 hours and then cooled to room temperature and shaken with 400 ml of dichloromethane, and the organic phase is washed with water, then with 10% strength aqueous sodium hydroxide solution and finally with 10% strength hydrochloric acid, then dried with sodium sulphate and filtered. From the filtrate, the solvent is carefully distilled off under reduced pressure.

This gives 17.7 g (82% of theory) of ethyl 2,4-dichloro-3-[2-(3-methylthio-4-methyl-5-oxo-1,2,4-triazolin-1-yl)-ethoxy]-benzoate as an oily residue (logP=$2,66^{a)}$).

The compound listed in Table 2 as Example (II-61) can be prepared, for example, as follows:

Example (II-61)

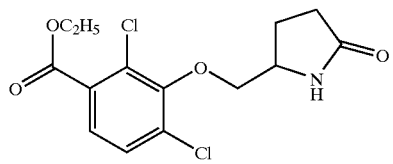

A mixture of 2.0 g (8.5 mmol) of ethyl 2,4-dichloro-3-hydroxy-benzoate, 3.6 g (12.75 mmol) of (S)-(+)-5-(p-tolylsulphonyloxymethyl)-pyrrolidin-2-one, 2.3 g (17 mmol) of potassium carbonate and 30 ml of acetonitrile is stirred at 76° C. for 13 hours, cooled to room temperature, diluted with water to about twice its original volume and shaken with methylene chloride. The organic phase is washed with saturated aqueous sodium chloride solution, dried with sodium sulphate and filtered. From the filtrate, the solvent is carefully distilled off under reduced pressure.

This gives 2.6 g (92% of theory) of ethyl (S)-2,4-dichloro-3-[(2-oxo-pyrrolidin-5-yl)-methoxy]-benzoate (logP=$2.14^{a)}$).

Use Examples

Example A

| Pre-emergence Test | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is sprayed with the preparation of active compound such that the particular amount of active compound desired is applied per unit area. The concentration of active compound in the spray liquor is chosen such that the particular amount of active compound desired is applied in 1000 liters of water per hectare.

After three weeks, the degree of damage to the plants is rated in % damage in comparison to the development of the untreated control. The figures denote:

0%=no effect (like untreated control)

100%=total destruction

In this test, for example, the compounds of Preparation Examples 1, 2, 3, 4, 5, 6, 7, 8, 9, 10 and 11 show strong activity against weeds, and most of them are tolerated well by crop plants, such as, for example, maize.

Example B

| Post-emergence Test | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants with a height of 5–15 cm are sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

In this test, for example, the compounds of Preparation Examples 1, 2, 3, 4, 5, 6, 7, 8, 9, 10, 11 and 13 show strong activity against weeds, and some are tolerated well by crop plants, such as for example, maize.

What is claimed is:

1. A substituted aryl ketone of the formula (I)

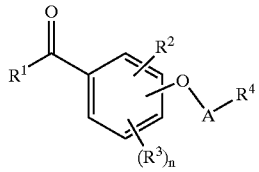

wherein n represents the number 0 or 1,

A represents alkanediyl (alkylene) having 1 to 6 carbon atoms, $R^1$ represents one of the groupings below

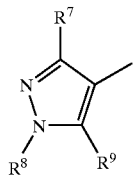

$R^2$ represents hydrogen, nitro, cyano, carboxyl, carbamoyl, thiocarbamoyl, halogen, or represents in each case optionally cyano-, halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkoxy, alkylthio, alkylsulphinyl, alkylsulphonyl, alkylamino, dialkylamino or dialkylaminosulphonyl having in each case 1 to 6 carbon atoms in the alkyl groups, $R^3$ represents nitro, cyano, carboxyl, carbamoyl, thiocarbamoyl, halogen, or represents in each case optionally cyano-, halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkoxy, alkylthio, alkylsulphinyl, alkylsulphonyl, alkylamino, dialkylamino or dialkylaminosulphonyl having in each case 1 to 6 carbon atoms in the alkyl groups, $R^4$ represents one of the heterocyclic groupings below

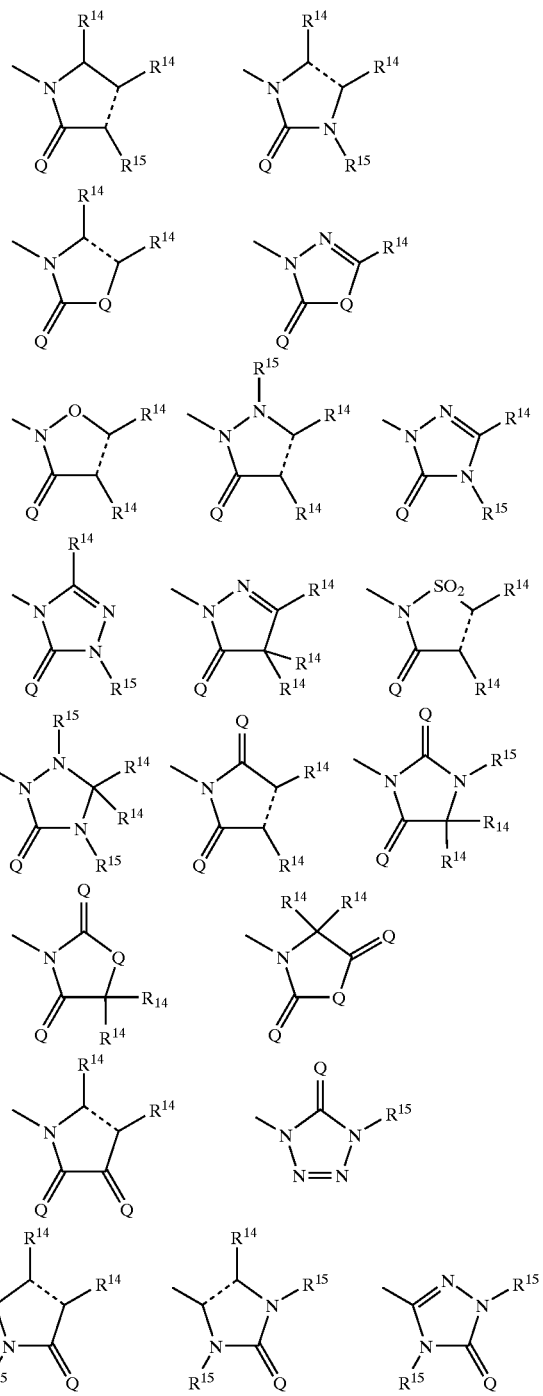

where in each case the broken bond is a single bond or a double bond,

Q represents oxygen or sulphur, $R^{14}$ represents hydrogen, hydroxyl, mercapto, cyano, halogen, represents in each case optionally cyano-, halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkylcarbonyl, alkoxy, alkoxycarbonyl, alkylthio, alkylsulphinyl or alkylsulphonyl having in each case up to 6 carbon atoms in the alkyl groups, represents in each case optionally halogen-substituted alkylamino or dialkylamino having in each case up to 6 carbon atoms in the alkyl groups, represents in each case optionally halogen-substituted alkenyl, alkinyl, alkenyloxy, alkenylthio or alkenylamino having in each case up to 6 carbon atoms in the alkenyl or alkinyl groups, represents in each case optionally halogen-substituted cycloalkyl, cycloalkyloxy, cycloalkylthio, cycloalkylamino, cycloalkylalkyl, cycloalkylalkoxy, cycloalkylalkylthio or cycloalkylalkylamino having in each case 3 to 6 carbon atoms in the cycloalkyl groups and optionally up to 4 carbon atoms in the alkyl moiety, or represents in each case optionally halogen-, $C_1$–$C_4$-alkyl- or $C_1$–$C_4$-alkoxy-substituted phenyl, phenyloxy, phenylthio, phenylamino, benzyl, benzyloxy, benzylthio or benzylamino, represents pyrrolidino, piperidino or morpholino, or—if two adjacent radicals $R^{14}$ and $R^{14}$ are located at a double bond—also together with the adjacent radical $R^{14}$ represents a benzo grouping, and $R^{15}$ represents hydrogen, hydroxyl, amino, alkylideneamino having up to 4 carbon atoms, represents in each case optionally halogen- or $C_1$–$C_4$-alkoxy-substituted alkyl, alkoxy, alkylamino, dialkylamino or alkaneoylamino having in each case up to 6 carbon atoms in the alkyl groups, represents in each case optionally halogen-substituted alkenyl, alkinyl or alkenyloxy having in each case up to 6 carbon atoms n the alkenyl or alkinyl groups, represents in each case optionally halogen-substituted cycloalkyl, cycloalkylalkyl or cycloalkylamino having in each case 3 to 6 carbon atoms in the cycloalkyl groups and optionally up to 3 carbon atoms in the alkyl moiety, or represents in each case optionally halogen-, $C_1$–$C_4$-alkyl- or $C_1$–$C_4$-alkoxy-substituted phenyl or benzyl, or together with an adjacent radical $R^{14}$ or $R^{15}$ represents optionally halogen- or $C_1$–$C_4$-alkyl-substituted alkanediyl having 3 to 5 carbon atoms, where the individual radicals $R^{14}$ and $R^{15}$—if more than one of them are attached to the same heterocyclic groupings—can have identical or different meanings within the scope of the above definition, $R^7$ represents hydrogen, cyano, carbamoyl, thiocarbamoyl, halogen, represents in each case optionally cyano-, halogen- or $C_1$–$C_4$-alkoxy-substituted alkyl, alkoxy, alkylthio, alkylsulphinyl, alkylsulphonyl or alkoxycarbonyl having in each case 1 to 6 carbon atoms in the alkyl groups, or represents optionally cyano-, halogen- or $C_1$–$C_4$-alkyl-substituted cycloalkyl having 3 to 6 carbon atoms, $R^8$ represents hydrogen, represents in each case optionally cyano-, halogen- or $C_1$–$C_4$-alkoxy-substituted alkyl having 1 to 6 carbon atoms, represents in each case optionally cyano- or halogen-substituted alkenyl or alkinyl having in each case 2 o 6 carbon atoms, represents in each case optionally cyano-, halogen- or $C_1$–$C_4$-alkyl-substituted cycloalkyl or cycloalkylalkyl having in each case 3 to 6 carbon atoms in the cycloalkyl group and optionally 1 to 4 carbon atoms in the alkyl moiety, or represents in each case optionally nitro-, cyano-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted aryl or arylalkyl having in each case 6 or 10 carbon atoms in the aryl group and optionally 1 to 4 carbon atoms in the alkyl moiety, $R^9$ represents hydroxyl, formyloxy, represents in each case optionally cyano-, halogen- or $C_1$–$C_4$-alkoxy substituted alkoxy, alkylcarbonyloxy, alkoxycarbonyloxy, alkylaminocarbonyloxy or alkylsulphonyloxy having in each case 1 to 6 carbon atoms in the alkyl groups, represents in each case optionally cyano- or halogen-substituted alkenyloxy or alkinyloxy having in each case 2 to 6 carbon atoms, or represents in each case optionally nitro-, cyano-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted arylalkoxy, arylcarbonyloxy, arylcarbonylalkoxy or arylsulphonyloxy having in each case 6 or 10 carbon atoms in the aryl group and otionally 1 to 4 carbon atoms in the alkyl moiety.

2. A compound of the formula (I) according to claim 1 wherein

A represents methylene, ethane-1,2-diyl (dimethylene), ethane-1,1-diyl, propane-1,2-diyl, propane-1,3-diyl (trimethylene), butane-1,2-diyl, butane-1,3-diyl or butane-1,4-diyl (tetramethylene), $R^2$ represents hydrogen, nitro, cyano, carboxyl, carbamoyl, thiocarbamoyl, fluorine, chlorine, bromine, iodine, or represents in each case optionally fluorine- and/or chlorine-, methoxy-, ethoxy-, n- or i-propoxy-, methyl- thio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, represents in each case optionally fluorine- and/or chlorine-, methoxy-ethoxy-, n- or i-propoxy-substituted methoxy, ethoxy, n- or i-propoxy, represents in each case optionally fluorine- and/or chlorine-substituted methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents methylamino, ethylamino, n- or i-propylamino, dimethylamino, diethylamino, dimethylaminosulphonyl or diethylaminosulphonyl, $R^3$ represents nitro, cyano, carboxyl, carbamoyl, thiocarbamoyl, fluorine, chlorine, bromine, represents in each case optionally fluorine- and/or chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, represents in each case optionally fluorine- and/or chlorine-, methoxy-, ethoxy-, n- or i-propoxy-substituted methoxy, ethoxy, n- or i-propoxy represents in each case optionally fluorine- an or chorine-substituted methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents methylamino, ethylamino, n- or i-propylamino, dimethylamino, diethylamino, dimethylaminosulphonyl or diethylaminosulphonyl, $R^4$ represents one of the heterocyclic groupings below,

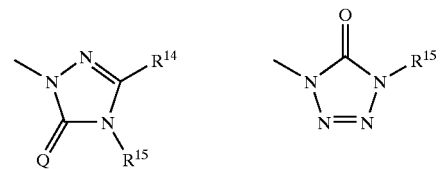

-continued

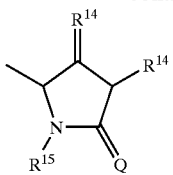 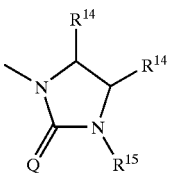

R⁷ represents hydrogen, cyano, carbamoyl, thiocarbamoyl, fluorine, chlorine, bromine, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methoxycarbonyl, ethoxycarbonyl, n- or i-propoxycarbonyl, or represents in each case optionally cyano-, fluorine-, chlorine-, bromine-, methyl- or ethyl-substituted cyclopropyl, cyclobutyl, cyclopentyl or cyclohexyl, R⁸ represents hydrogen, represents in each case optionally cyano-, fluorine-, chlorine-, bromine-, methoxy- or ethoxy-substituted methyl, ethyl, n- or i-propyl, n-, i-, s- or t-butyl, represents in each case optionally cyano-, fluorine-, chlorine- or bromine-substituted propenyl, butenyl, propinyl or butinyl, represents in each case optionally cyano-, fluorine-, chlorine-, bromine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally nitro-, cyano-, fluorine-, chlorine-, bromine-, methyl-, ethyl-, n- or i-propyl, n-, i-, s- or t-butyl, trifluoromethyl, methoxy, ethoxy, n- or i-propoxy, n-, i-, s- or t-butoxy-, difluoromethoxy- or trifluoromethoxy-substituted phenyl or benzyl, R⁹ represents hydroxyl, formyloxy, represents in each case optionally cyano-, fluorine-, chlorine-, bromine-, methoxy-, ethoxy-, n- or i-propoxy-substituted methoxy, ethoxy, n- or i-propoxy, n-, i-, s- or t-butoxy, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents in each case optionally cyano-, fluorine-, chlorine- or bromine-substituted propenyloxy, butenyloxy, propinyloxy or butinyloxy, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substitute phenylmethoxy, benzoyloxy, benzoylmethoxy or phenylsulphonyloxy, R¹⁴ represents hydrogen, hydroxyl, mercapto, cyano, fluorine, chlorine, bromine, iodine, represents in each case optionally fluorine-, chlorine-, methoxy-, ethoxy-, n- or i-propoxy-, n-, i-, s- or t-butoxy-, methylthio-, ethylthio-, n- or i-propylthio-, n-, i-, s- or t-butylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, represents methylamino, ethylamino, n- or i-propylamino, n-, i-, s- or t-butylamino, dimethylamino, diethylamino, di-n-propylamino or di-i-propylamino, represents in each case optionally fluorine- and/or chlorine-substituted ethenyl, propenyl, butenyl, ethinyl, propinyl, butinyl, propenyloxy, butenyloxy, propenylthio, butenylthio, propenylamino or butenylamino, represents in each case optionally fluorine- and/or chlorine-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or represents in each case optionally fluorine-, chlorine-, methyl-, ethyl-, n- or i-propyl-, n-, i-, s or t-butyl-, methoxy-, ethoxy-, n- or i-propoxy-substituted phenyl, phenyloxy, phenylthio, phenylamino, benzyl, benzyloxy, benzylthio or benzylamino, represents pyrrolidino, piperidino or morpholino, or—if two adjacent radicals R¹⁴ and R¹⁴ are located at a double bond—together with the adjacent radical R¹⁴ also represents a benzo grouping, and R¹⁵ represents hydrogen, hydroxyl, amino, represents in each case optionally fluorine- and/or chlorine-, methoxy- or ethoxy-substituted methyl, ethyl, n- or i-propyl, n-, i- or s-butyl, methoxy, ethoxy, n- or i-propoxy, methylamino, ethylamino or dimethylamino, represents in each case optionally fluorine- and/or chlorine-substitute ethenyl, propenyl, ethinyl, propinyl or propenyloxy, represents in each case optionally fluorine- and/or chlorine-substituted cyclopropyl, cyclobutyl, cyclopentyl, cyclohexyl, cyclopropylmethyl, cyclobutylmethyl, cyclopentylmethyl, cyclohexylmethyl, or represents in each case optionally fluorine-, chlorine-, methyl-, ethyl-, n- or i-propyl-, n-, i-, s- or t-butyl-, methoxy-, ethoxy-, n- or i-propoxy-substituted phenyl or benzyl, or together with an adjacent radical R¹⁴ or R¹⁵ represents in each case optionally methyl- and/or ethyl-substituted propane-1,3-diyl (trimethylene) or butane-1,4-diyl (tetramethylene).

3. A compound of the formula (I) according to claim 1 wherein

A represents methylene or dimethylene,

R² represents hydrogen, nitro, cyano, fluorine, chlorine, bromine, iodine, methyl, ethyl, difluoromethyl, trifluoromethyl, dichloromethyl, trichloromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl, R³ represents nitro, cyano, fluorine, chlorine, bromine, iodine, methyl, ethyl, difluoromethyl, trifluoromethyl, dichloromethyl, trichloromethyl, methoxymethyl, methylthiomethyl, methylsulphinylmethyl, methyl sulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl, $R^7$ represents hydrogen, cyano, fluorine, chlorine, bromine, represents in each case optionally fluorine-, chlorine-, methoxy- or ethoxy-substituted methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, methoxycarbonyl, ethoxycarbonyl, n- or i-propoxycarbonyl, $R^8$ represents hydrogen, represents in each case optionally cyano-, fluorine-, chlorine-, methoxy- or ethoxy-substituted methyl, ethyl, n- or i-propyl, represents in each case optionally fluorine- or chlorine-substituted propenyl or propinyl, represents optionally fluorine-, chlorine-, bromine-, methyl- or ethyl-substituted cyclopropyl, or represents in each case optionally fluorine-, chlorine-, bromine-, methyl-, ethyl-, n- or i-propyl-, trifluoromethyl-, methoxy-, ethoxy-, n- or i-propoxy-, difluoromethoxy- or trifluoromethoxy-substituted phenyl or benzyl, $R^9$ represents hydroxyl, formyloxy, represents in each case optionally cyano-, fluorine-, chlorine-, bromine-, methoxy-, ethoxy-, n- or i-propoxy-substituted methoxy, ethoxy, n- or i-propoxy, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represent propenyloxy or propinyloxy, or represents in each case optionally nitro-, cyano-, fluorine-, chlorine-, bromine-, methyl-, ethyl-, n- or i-propyl-, trifluoromethyl-, methoxy-, ethoxy-, n- or i-propoxy-, difluoromethoxy- or trifluoromethoxy-substituted phenylmethoxy, benzoyloxy, benzoylmethoxy or phenylsulphonyloxy, $R^{14}$ represents hydrogen, hydroxyl, mercapto, cyano, fluorine, chlorine, bromine, iodine, represents in each case optionally fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, represents methylamino, ethylamino, n- or i-propylamino, dimethylamino or diethylamino, represents in each case optionally fluorine- and/or chlorine-substituted ethenyl, propenyl, ethinyl, propinyl, propenyloxy, propenylthio or propenylamino, represents in each case optionally fluorine- and/or chlorine-substituted cyclopropyl, cyclopropyloxy, cyclopropylamino, cyclopropylmethyl, cyclopropylmethoxy or cyclopropylmethylamino, or represents in each case optionally fluorine-, chlorine-, methyl-, ethyl-, n- or i-propyl-, methoxy-, ethoxy-, n- or i-propoxy-substituted phenyl, phenyloxy, phenylthio, phenylamino, benzyl, benzyloxy, benzylthio or benzylamino, or—if two adjacent radicals $R^{14}$ and $R^{14}$ are located at a double bond—together with the adjacent radical $R^{14}$ also represents a benzo grouping, and $R^{15}$ represents hydrogen, hydroxyl, amino, represents in each case optionally fluorine- and/or chlorine-, methoxy- or ethoxy-substituted methyl, ethyl, n- or i-propyl, methoxy, ethoxy, n- or i-propoxy, methylamino, ethylamino or dimethylamino, represents propenyl or propinyl, represents in each case optionally fluorine- an or chlorine-substituted cyclopropyl, cyclobutyl or cyclopropylmethyl, or represents in each case optionally fluorine-, chlorine-, methyl-, ethyl- n- or i-propyl-, methoxy-, ethoxy-, n- or i-propoxy-substituted phenyl or benzyl, or together with an adjacent radical $R^{14}$ or $R^{15}$ represent in each case optionally methyl- and/or ethyl-substituted propane-1,3-diyl (trimethylene) or butane-1,4-diyl (tetramethylene).

4. A process for preparing a compound of the formula (I) according to claim 1 comprising the step of:

(a) reacting a substituted benzoic acid of the formula (II)

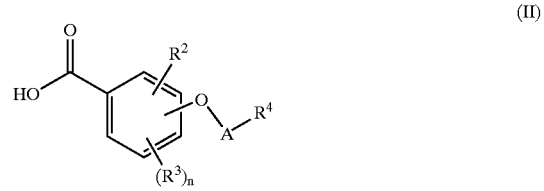

(II)

wherein n, A, $R^2$, $R^3$ and $R^4$ are each as defined in claim 1, or reactive derivatives thereof said reactive deriviatives optionally being selected from the group consisting of corresponding acid halides, acid cyanides and esters with a compound of the formula (III)

$R^1$–H           (III)

wherein $R^1$ is as defined in claim 1, optionally in the presence of a dehydrating agent, optionally in the presence of one or more reaction auxiliaries and optionally in the presence of a diluent, or (b) reacting a substituted benzoyl ketone of the formula (Ia)

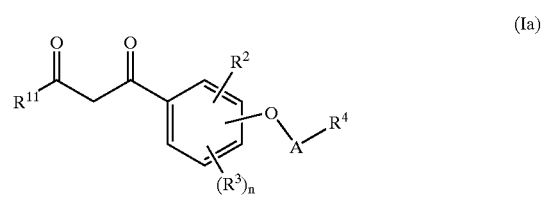

(Ia)

wherein n, A, $R^2$, $R^3$, and $R^4$—are each as defined in claim 1, $R^{11}$ represents hydrogen, represents optionally cyano-, halogen- or $C_1$–$C_4$-alkoxy-substituted alkyl having 1 to 6 carbon atoms or represents optionally cyano-, halogen- or $C_1$–$C_4$-alkyl-substituted cycloalkyl having 3 to 6 carbon atoms, with an orthoformic ester or a N,N-dimethyl-formamide acetal or with a cyanoformic ester or with carbon disulphide and an alkylating agent, and then with hydroxylamine or an acid adduct thereof, optionally in the presence of one or more reaction auxiliaries and optionally in the presence of one or more diluents, and, optionally, following the the step of said process (a) or said process (b) according to the invention, subjecting the resulting compound the formula (I) to on or more substitution, oxidation or reduction reactions within the scope of the definition of the substituents and/or converting the compounds of the formula (I) into salt-like compounds.

5. A method for controlling one or more undesirable plants, comprising the step of applying at least one compound of the formula (I) according to claim 1 to said one or more undesirable plants and/or their habitats.

* * * * *